US012740787B2

(12) United States Patent
Ravikumar

(10) Patent No.: US 12,740,787 B2
(45) Date of Patent: Sep. 22, 2026

(54) CATHETER DEVICE AND METHOD FOR SELECTIVE OCCLUSION OF ARTERIES OF THE DESCENDING AORTA OR ILIAC VASCULATURE

(71) Applicant: Sundaram Ravikumar, Dobbs Ferry, NY (US)

(72) Inventor: Sundaram Ravikumar, Briarcliff Manor, NY (US)

( * ) Notice: Subject to any disclaimer, the term of this patent is extended or adjusted under 35 U.S.C. 154(b) by 232 days.

(21) Appl. No.: 18/267,774

(22) PCT Filed: Jan. 18, 2022

(86) PCT No.: PCT/US2022/012833
§ 371 (c)(1),
(2) Date: Jun. 15, 2023

(87) PCT Pub. No.: WO2022/133502
PCT Pub. Date: Jun. 23, 2022

(65) Prior Publication Data

US 2024/0090901 A1 Mar. 21, 2024

Related U.S. Application Data

(60) Provisional application No. 63/126,225, filed on Dec. 16, 2020.

(51) Int. Cl.

| | |
|---|---|
| ***A61B 17/12*** | (2006.01) |
| ***A61M 25/09*** | (2006.01) |
| ***A61M 25/10*** | (2013.01) |

(52) U.S. Cl.
CPC .... *A61B 17/12136* (2013.01); *A61B 17/1204* (2013.01); *A61B 17/12109* (2013.01);
(Continued)

(58) Field of Classification Search
CPC .......... A61B 17/1204; A61B 17/12109; A61B 17/12136; A61B 2017/12004; A61F 2/07;
(Continued)

(56) References Cited

U.S. PATENT DOCUMENTS

| | | | | |
|---|---|---|---|---|
| 6,196,230 B1 * | 3/2001 | Hall | A61M 25/10 | 606/108 |
| 2003/0097036 A1 * | 5/2003 | St. Germain | A61M 25/003 | 600/16 |

(Continued)

*Primary Examiner* — Jocelin C Tanner
(74) *Attorney, Agent, or Firm* — Theresa O'Rourke Nugent; Law Office of Theresa O'Rourke Nugent

(57) ABSTRACT

An improved catheter device for selectively isolating and occluding a portion of the descending aorta and/or the iliac vasculature of a patient, including a guiding or isolating component on a distal end of an elongate hollow catheter shaft which is advanceable though the vascular system of the patient. The catheter shaft has a proximal portion that extends out from the patient and a distal portion adapted to be disposed within the vasculature of the patient. The guiding or isolating component as well as a plurality of expandable members are disposed on the distal portion. A number of expandable members are positioned on the catheter with dimensions and configured so that when expanded it rests within a target artery or vasculature to occlude blood flow. Other expandable members may be spaced apart from the isolating or fixation member and configured to selectively isolate and occlude blood flow through different portions of target arteries and other vasculature.

8 Claims, 20 Drawing Sheets

(52) U.S. Cl.
CPC .............. *A61B 2017/12004* (2013.01); *A61M 2025/09141* (2013.01); *A61M 25/1011* (2013.01); *A61M 2025/1061* (2013.01)

(58) Field of Classification Search
CPC ............... A61F 2/958; A61M 25/0032; A61M 25/0026; A61M 25/0097; A61M 25/09; A61M 25/1002; A61M 25/1011; A61M 25/10184; A61M 25/104; A61M 2025/0036; A61M 2025/004; A61M 2025/09141; A61M 2025/09175; A61M 2025/1052; A61M 2025/1061
USPC .......................................................... 606/194
See application file for complete search history.

(56) References Cited

U.S. PATENT DOCUMENTS

| | | | | |
|---|---|---|---|---|
| 2009/0182245 | A1* | 7/2009 | Zambelli | A61M 25/09041 600/585 |
| 2011/0034948 | A1* | 2/2011 | Ravikumar | A61M 25/1011 606/194 |
| 2012/0029478 | A1* | 2/2012 | Kurosawa | A61M 25/09 604/528 |
| 2015/0105816 | A1* | 4/2015 | Rasmusson | A61B 17/12163 606/194 |
| 2016/0228684 | A1* | 8/2016 | Martin | A61M 25/04 |
| 2018/0243536 | A1* | 8/2018 | von Segesser | A61M 25/09025 |
| 2019/0240461 | A1* | 8/2019 | Dayton | A61M 25/0136 |
| 2019/0314109 | A1* | 10/2019 | Brucker | A61B 18/00 |

* cited by examiner 100
102
106
110
105
116

115
102
112
114A
114B
114C
114D

FIG. 19A
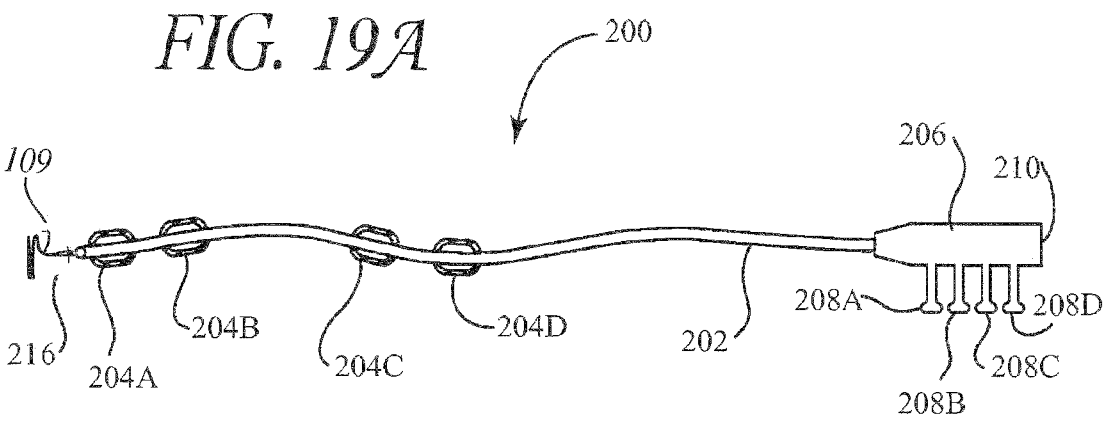
FIG. 19B
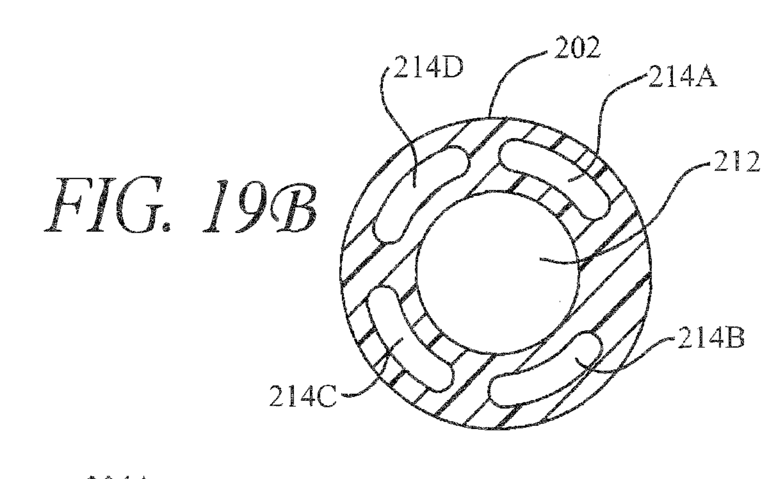
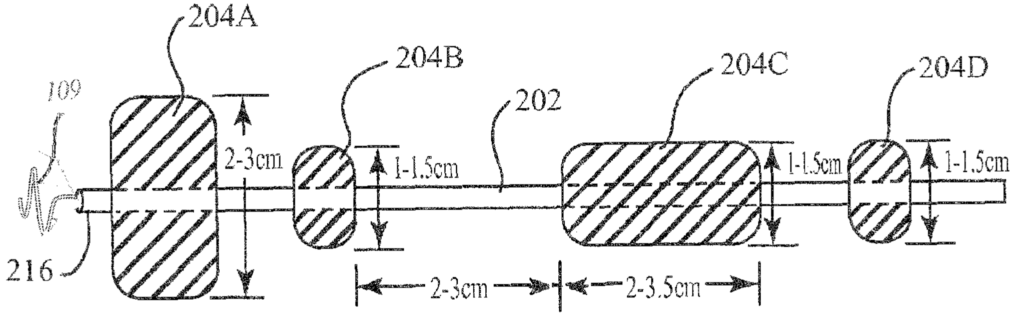
FIG. 19C

CATHETER DEVICE AND METHOD FOR SELECTIVE OCCLUSION OF ARTERIES OF THE DESCENDING AORTA OR ILIAC VASCULATURE

RELATED APPLICATIONS

The present application claim priority from PCT application Serial No. PCT/US/12833 entitled "Catheter Device and Method for Selective Occlusion of Arteries of the Descending Aorta or Iliac Vasculature" and provisional application Ser. No. 63/126,225 filed Dec. 16, 2020 entitled "Catheter Device and Method for Selective Occlusion of Arteries of the Descending Aorta", the entire contents of which are hereby incorporated herein by reference for all purposes.

BACKGROUND OF THE INVENTION

Field of the Invention

This invention relates broadly to occlusion catheter devices and associated methods for vascular applications. More particularly, this invention relates to aortic occlusion catheter devices and associated methods as well as iliac occlusion catheter devices and associated methods of use.

State of the Art

In many trauma situations and even during surgical procedures at a medical facility, it may be difficult to isolate the injury that is the cause of the loss of blood or even just isolate the artery or vein based on the location within the body. In these situations, maintaining blood flow to the heart, neck and lungs while temporarily blocking the flow of blood through the aorta may be necessary to stabilize the patient and provide time for interventional treatment.

An example of such treatment is described in U.S. Pat. No. 5,820,593 wherein an aortic balloon catheter is inserted into the femoral artery and guided into position in the aorta of the patient. The balloon catheter includes two balloons, a distal balloon and a proximal balloon. The distal balloon is positioned in the ascending aorta just above the aortic valve. The proximal balloon is positioned in the descending aorta below the brachiocephalic trunk. When only the proximal balloon is inflated, a supply of blood is delivered to the arteries of the head and heart while blocking the flow of blood below the thorax, thereby providing hemostasis in severe hemorrhage below the thorax. However, these prior art devices and treatments require opening the intra-abdominal cavity and manually inspecting the arteries of the intra-abdominal cavity (many of which are hidden behind the organs therein) in order to identify the root cause of the hemorrhage. Once the cause of the hemorrhage is identified, the injured artery is clamped upstream from the injury. These steps are typically time consuming and can be problematic, especially when there is severe bleeding. In these cases, the lack of blood flowing below the thorax can result in renal failure or damage to other parts of the body that rely on blood flowing below the thorax.

Co-owned U.S. Pat. Nos. 8,211,138 and 7,771,448 include a number of expandable members, such as four inflatable balloons, along a catheter shaft however the distal end of the catheter shaft can become lodged into one of the visceral artery origins causing damage. Further, the catheter can migrate into one of the visceral artery origins resulting in complications or bleeding issues. Again, time is of the essence at such incidents and even a second or millisecond where the catheter migrates and has to be withdrawn then re-inserted can result in further uncontrolled bleeding. Further, during a kidney operation or other abdominal surgical procedure time is also important so any migration of the distal end of the catheter can have a tremendous impact on the overall viability or success of the surgical procedure.

Thus, there remains a need in the art to provide devices and treatments that provide for quick identification and isolation of an injured artery below the thorax without migration of the catheter or complications, thereby stabilizing the patient and providing time for interventional treatment.

Further, the current art includes either just one balloon to occlude an artery or a set stationary number of balloons on a catheter. A need exists for varying location of a multiple of balloons on a catheter which may function to occlude an artery or function to isolate an artery or vein within the body. Another need is for one or many balloons which can move along a catheter so as each balloon may be spaced apart from another balloon at different lengths and locations on the catheter. Another need exists for a guiding balloon or other component such as a guidewire to prevent migration of the distal end of the catheter during use. These and other needs may be met by the inventive improved catheter and methods of use.

By way of a further example, the surgical procedure of a kidney transplantation requires the isolation and occlusion of certain arteries such as renal arteries. During a kidney transplantation the recipient patient waiting for the donor kidney (whether from a deceased-donor (cadaveric) or living-donor transplantation) does not have his or her existing damaged kidneys removed because this has been shown to increase the rates of surgical morbidities, and the donor kidney is placed inferior of the normal anatomical location (often in the iliac fossa). As a result, it is often necessary to use a different blood supply for the donor kidney. Typically, the renal artery of the donor kidney, previously branching from the abdominal aorta in the donor, is connected by an anastomosis to the external iliac artery in the recipient, and the renal vein of the donor kidney, previously draining to the inferior vena cava in the donor, is connected by an anastomosis to the external iliac vein in the recipient. Most conventional techniques for vascular anastomosis require the interruption of blood flow through the receiving vessel while the anastomosis is performed. Such interruption of blood flow is typically accomplished by clamping the receiving vessel. In the event that calcium plaque has built up at the clamping location, the clamping can cause the receiving vessel to bleed at the clamp site. Such bleeding is very difficult to repair. Moreover, the clamping can dislodge plaque and it can be carried to the foot or brain as an embolism. In the foot, the embolism can cause gangrene. In the brain, the embolism can cause a stroke. Thus, there exists a need to isolate or occlude the blood flow without clamping and thus reducing the risk of embolism.

The devices, methods, assemblies and systems of the subject invention provide benefits and advantages that may overcome a number of problems with respect to known catheters and devices, particularly the problems that arise due to the difficulty of migration of the distal end of the catheter when in use within the patient's body.

SUMMARY OF THE INVENTION

It is therefore an object of the invention to provide a surgical device (and corresponding method of treatment)

that enables quick identification and isolation of an artery anywhere in the body thereby allowing the attending physician to stop bleeding or to perform a surgical procedure on the isolated area. The present invention provides an endoscopic device and method for isolating a site, such as the descending aorta, iliac bifurcation, celiac artery, superior mesenteric and renal arteries, inferior mesenteric artery, left or right external iliac arteries or any other arterial location within the body. The inventive device is placed within the body through a small, percutaneous penetration in the patient. The inventive device allows the surgeon to guide the device through the vasculature of the patient via a guiding member and then position an anchor or isolating balloon within a location above or further within the artery from the target surgical site, then place a first or distal isolation or guide component such as a balloon or guidewire (by way of non-limiting example only) on one end of the target surgical site and a second proximal balloon on a second end of the target surgical site, which upon inflation of each balloons isolates the target surgical site from blood flood and occludes the target surgical site. Multiple balloons may be employed depending on the target arteries and surgical procedure being employed. The system is particularly suited for occluding and isolating a coronary artery or an internal mammary artery in a thoracoscopic coronary artery procedure. While being especially suited for thoracoscopic procedures, the system and method of the invention are also useful in other surgical procedures, such as laparoscopic, endoscopic and arthroscopic procedures, as well as in conventional open surgical procedures to stabilize the patient and provide time for interventional treatment. For example, the inventive device and methods are useful in a kidney transplant or other surgical procedure regarding the iliac vasculature. Other surgical procedures may also use the inventive device and methods.

It is another object of the invention to provide a surgical device (and corresponding method of treatment) that enables quick identification and isolation of a hemorrhaging artery in the abdomen/pelvis without requiring that the abdominal cavity be opened for inspection and clamping and without migration of the catheter into a visceral artery origin.

It is a further object of the invention to provide a surgical device (and corresponding method of treatment) that selectively occludes the arteries flowing from the abdominal aorta in a manner that stabilizes the blood pressure of the patient while maintaining blood flow through arteries that are upstream from the hemorrhage.

It is also an object of the invention to provide a surgical device (and corresponding method of treatment) that is quickly and effectively located (e.g., secured in place) in the abdominal aorta of the patient.

In accord with these objects, which will be discussed in detail below, an improved catheter device for accessing the abdominal aorta of a patient includes an elongate hollow catheter shaft which is advanceable through the arterial system of the patient. The catheter shaft has a proximal portion that extends out from the patient and a distal portion adapted to be disposed within the abdominal aorta of the patient. A plurality of expandable members is disposed on the distal portion including one guiding member on the distal end of the distal portion. The distal end guiding member may be a guidewire or an expandable member which is smaller in diameter than the other expandable members when the distal end is being inserted within the aorta and in one embodiment the distal end in one embodiment the guide expandable member can be further expanded to the same diameter as the other expandable members or in yet another embodiment further expanded to an even larger diameter than the other expandable members. One expandable member is dimensioned and configured so that it rests within the iliac bifurcation of the abdominal aorta when expanded so as to secure the catheter and minimize catheter movement within the abdominal aorta of the patient once deployed in an active expanded state. At least two other expandable members are spaced apart from the guiding member, whether a guidewire or an expandable member, and configured to selectively occlude blood flow to different arteries that extend from the abdominal aorta when expanded. Preferably, the distal-most and the proximal-most expandable members are spaced apart at a distance of more than 10 cm and less than 60 cm, or more than 15 cm and less than 50 cm, or most preferably on the order of more than 20 cm and less than 40 cm).

The improved catheter device of the present invention can be quickly fixated within the abdominal aorta and manipulated in order to efficiently identify and isolate a hemorrhage flowing from an abdominal artery with reduced risk of migration while being inserted into the aorta. In addition, the improved catheter device can be used in treating an abdominal aortic aneurysm.

According to a preferred embodiment of the invention, the expandable members which are not the farthest distal expandable member are realized by at least two to four inflatable balloons or preferably two to three inflatable balloons, each of the balloons no matter the number of balloons is controlled by fluidic pressure supplied thereto via corresponding inflation lumens in the elongate catheter shaft. In an embodiment with three expandable balloons each are independently inflatable to a diameter of at least 2.5 cm with the farthest distal balloon inflatable to a diameter of at least 0.5 cm, and the catheter shaft has an external diameter in a range between 5 and 9 french with a total length of at least 50 cm but could be as long as 90 cm. In another embodiment the number of balloons is five. In yet another embodiment the number of balloons is four. Any combination of balloons as expandable members may be employed from one to ten or more expandable members such as balloons.

In another embodiment of the present invention, the invention includes a guidewire comprised of nitinol that is capable of extending out of the catheter on the distal end and forming a corkscrew like configuration or a spiral like configuration and the expandable members are realized by at least four inflatable balloons controlled by fluidic pressure supplied thereto via corresponding inflation lumens in the elongate catheter shaft. The four balloons are independently inflatable to a diameter of at least 2.5 cm and the catheter shaft has an external diameter in a range between 7 and 9 trench with a total length of at least 80 cm. In yet another embodiment of the present invention the guidewire extends out of the catheter which only has three expanded members such as balloons inflatable to a diameter of at least about 0.5 cm to about 2.5 cm as the lower diameter but can expand to a higher diameter up to 5.0 cm.

In another embodiment of the present invention, it is an object of the invention to provide a minimally invasive surgical device (and corresponding method of treatment) that enables selective isolation and occlusion of blood flow through the iliac vasculature suitable for preparing a portion of the iliac vascular for an anastomosis as part of a kidney transplantation. Further, it is another object of the invention to provide such a minimally invasive surgical device (and corresponding method of treatment) that employs a catheter device introduced percutaneously through the femoral vasculature. It is a further object of the invention to provide a surgical device (and corresponding method of treatment) that selectively isolates and occludes a portion of one branch of the iliac vasculature while maintaining blood flow through the other branch of the iliac vasculature and through the abdominal vasculature to the heart. In addition, it is also an object of the invention to provide such a minimally invasive surgical device (and corresponding method of treatment) that is quickly and effectively located (e.g., secured in place) in the iliac vasculature of the patient.

In accord with these objects, which will be discussed in detail below, this embodiment of an improved catheter device for selectively isolating and occluding a portion of the iliac vasculature of a patient includes an elongate hollow catheter shaft which is advanceable though the vascular system of the patient. The catheter shaft has a proximal portion that extends out from the patient and a distal portion adapted to be disposed within the iliac vasculature of the patient. A guiding member and a plurality of expandable members are disposed on the distal portion of the catheter. The guiding member may be for example a guidewire or one expandable member. If the guiding member is an expandable member such as a balloon then it is dimensioned and configured to be of a diameter larger than the diameter of the catheter but smaller than a second expandable member, or larger than the second expandable member. If the guiding member is an expandable member which will also function as a securing or fixation member within the iliac bifurcation, then such expandable member is dimensioned and configured so that when fully expanded it rests within the bifurcation of the descending aorta to the common iliac arteries (and/or within the bifurcation of the inferior vena cava that leads to the common iliac veins) so as to fixate the catheter within the iliac vasculature of the patient. At least one or two other expandable members are spaced apart from the most distal member and configured to selectively isolate and occlude blood flow through different portions of the iliac vasculature.

In this embodiment the improved catheter device of the present invention can be quickly fixated within the iliac vasculature and manipulated in order to efficiently isolate and occlude a portion of the iliac vasculature (preferably a portion of the common iliac artery or common iliac vein of the patient). Such isolation and occlusion are suitable for preparing the isolated iliac vascular portion for an anastomosis as part of a kidney transplantation procedure. According to this further embodiment of the invention, the expandable members are realized by inflatable balloons controlled by fluidic pressure supplied thereto via corresponding inflation lumens in the elongate catheter shaft. The balloons are independently inflatable by supply of fluidic pressure thereto. In the preferred embodiment, there are two balloons positioned proximally relative to the seating balloon and spaced apart from one another by a length in the range between 2 cm and 3 cm. In this embodiment of the present invention, one of these balloons has a length in its inflated state in the range between 2 cm and 3.5 cm such that it extends over the bifurcation point of the common iliac artery (or vein) to the external and internal arteries (or veins). Moreover, these two balloons preferably have a maximum diameter dimension in the range of about 0.5 cm to about 2.5 cm, which ensures that the balloons sealably contact the vessel wall of the iliac vasculature in their inflated state. The catheter shaft has an external diameter in a range between 5 and 9 french with a total length of at least 50 cm, though the total length may vary depending on the height of the patient and other factors.

Additional objects and advantages of the invention will become apparent to those skilled in the art upon reference to the detailed description taken in conjunction with the provided figures and various embodiments as well as disclosures herein.

BRIEF DESCRIPTION OF THE DRAWINGS

FIG. 8B is an exploded view of balloon 104A showing the two inflation states.

FIG. 8C is a cross-sectional view of the catheter shaft of the catheter device of FIG. 8A.

FIGS. 9A and 9B are side views of the catheter device of FIG. 8 wherein FIG. 9A shows the distal end expandable member in the first inflation state with half inflation, and FIG. 9B shows the distal end expandable member in the second inflation state in full inflation.

FIGS. 11A and 11B are side view of the catheter device of FIG. 10 and cross-sectional view of the catheter shaft of the catheter device wherein FIG. 11A is a side view and FIG. 11B is a cross-sectional view of the catheter shaft.

FIG. 19A is a side view of another illustrative embodiment of a catheter device in accordance with the present invention for use in the iliac vasculature such as when used in a kidney transplantation including a guidewire and four expandable members or balloons.

FIG. 19B is a cross-sectional view of the catheter shaft of the catheter device of FIG. 19A.

FIG. 19C is a schematic illustration of the size and spacing of the inflatable balloon members of the catheter device of FIGS. 19A and 19B.

DETAILED DESCRIPTION OF THE INVENTION

The descriptive terms "downstream" and "upstream", when used herein in relation to the patient's vasculature, relate to the direction of normal blood flow and to the direction opposite normal blood flow, respectively, i.e., "upstream" is closer to the heart in the arterial system.

In addition, the terms "proximal" and "distal", when used in relation to instruments used in a surgical procedure refer to directions closer and farther away, respectively, from that end of the instrument which is held or manipulated by the operator performing the procedure. The proximal end of the catheter is the portion of the device which is outside of the patient's body and the distal end is the portion of the catheter within the inside of the patient's body or vasculature. The dimensions of the expandable members such as balloons are in nominal dimensions, including the various ranges provided.

Figure 1:
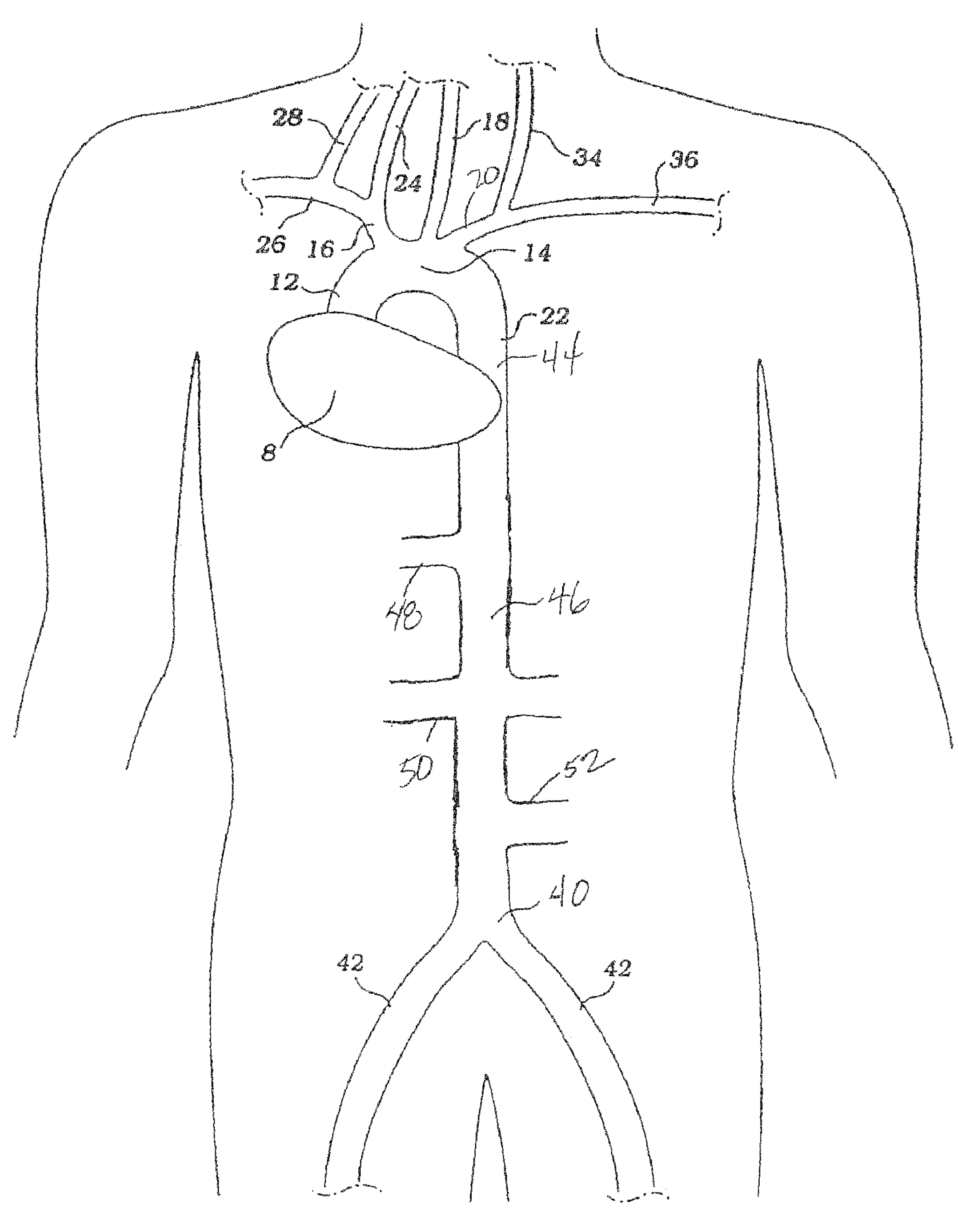
FIG. 1 is a schematic illustration of the principal arteries of the human body.

The principal arteries of the human body are shown in FIG. 1. During systole, oxygenated blood leaves the heart 8 and enters the aorta 10. The aorta 10 includes the ascending aorta 12, the aortic arch 14, and the descending aorta 22. The aortic arch 14 leads to the brachiocephalic trunk 16, the left common carotid artery 18, and the left subclavian artery 20. The brachiocephalic trunk 16 branches into the right common carotid artery 24 and the right subclavian artery 26. The right and left subclavian arteries 26, 20 give rise to the right vertebral artery 28 and the left vertebral artery 34, respectively in addition to the right axillary artery 26 and the left axillary artery 36, respectively. The descending aorta 22 starts after the aortic arch 14 and ends at the iliac bifurcation 40, which is a branch that splits into the two common iliac arteries 42 that go to the legs.

The descending aorta 22, by convention, is subdivided into the thoracic aorta 44 and the abdominal aorta 46. The thoracic aorta 44 runs from the aortic arch 14 to the diaphragm and gives off numerous branches that supply oxygenated blood to the chest cage and the organs within the chest. The abdominal aorta 46 begins at the diaphragm as a continuation of the thoracic aorta 44 and runs down to the iliac bifurcation 40. The abdominal aorta supplies oxygenated blood to all of the abdominal and pelvic organs and the legs.

Figure 20:
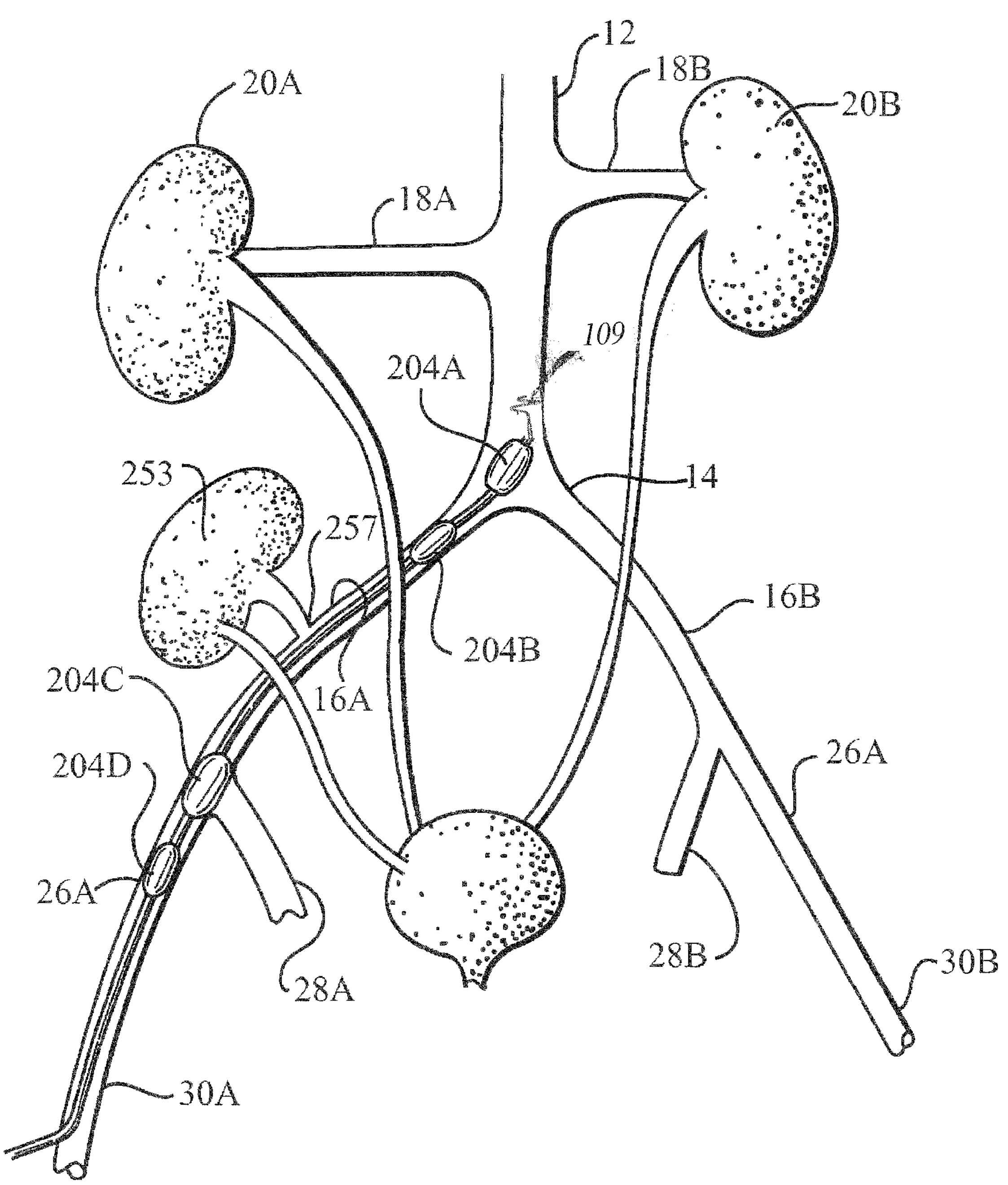
FIG. 20 is a schematic illustration of the arterial system and venous system of the abdomen of the human body, respectively, including the iliac vasculature and is an illustration showing the advancement and placement of the catheter device of FIG. 19A into the iliac arterial vasculature for selectively isolating and occluding a portion of one branch of the iliac arterial vasculature in accordance with the present invention; with an anastomosis from the isolated portion of the iliac vasculature to a donor kidney as part of a kidney transplantation procedure in accordance with the present invention.

The abdominal aorta 46 leads to the celiac artery 48, the superior mesenteric and renal arteries 50, and the inferior mesenteric artery 52. The celiac artery 48 is a short thick branch of artery about an inch in length that divides into three branches, the gastric, hepatic, and splenic arteries. The celiac artery 48 supplies blood to the intestines, spleen, and liver. The superior mesenteric artery supplies blood to the intestines, and the renal arteries 18A, 18B supply blood to the kidneys 20A, 20B as shown in FIG. 20. The inferior mesenteric artery 52 supplies blood to the colon and the rectum.

Figure 2A:
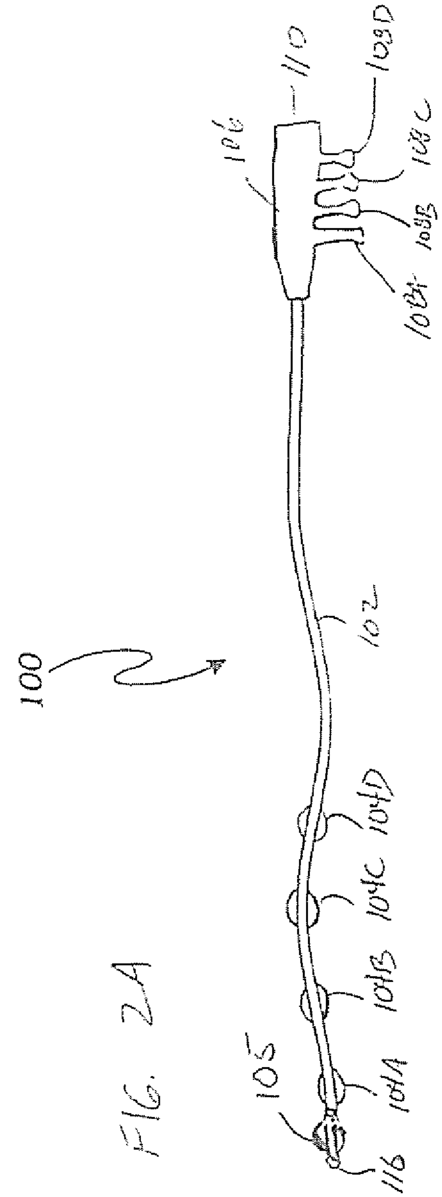
FIG. 2A is a side view of an illustrative embodiment of one embodiment of a catheter device in accordance with the present invention including five expandable members.
Figure 2B:
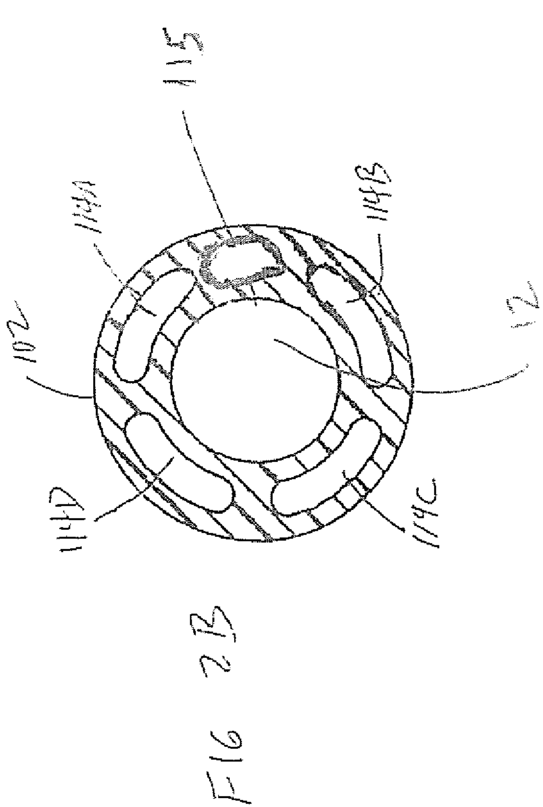
FIG. 2B is a cross-sectional view of the catheter shaft of the catheter device of FIG. 2A.

FIGS. 2A and 2B depict one embodiment of the present invention including an improved catheter device 100. The device 100 includes a hollow elongate catheter shaft 102 with four distally mounted expandable occlusion balloons 104A, 104B, 104C, 104D in this embodiment though the number of expandable members can range from one to five or more. The four occlusion balloons in this embodiment are spaced apart along the distal portion of the shaft 102. Preferably, the four occluding balloons are expandable to a maximum diameter of approximately 0.5 to 3.0 cm, and the spacing between adjacent balloons is regular at a distance of approximately 10 cm. In this configuration, there is a distance on the order of approximately 30 cm between the first balloon 104A and the fourth balloon 104D. These dimensions correspond to the configuration and spacing of the major arteries (e.g., the celiac artery 48, renal arteries and superior mesenteric artery 50, inferior mesenteric artery 52, iliac bifurcation 40) of the abdominal aorta 46 as will become evident from the operation of the catheter device 100 as set forth below. The spacing between each of the expandable members or balloons may vary depending on the height of the patient in that there may be a smaller distance or larger distance from by way of example the celiac artery 48 and the iliac bifurcation 40. Later embodiments of the instant invention show the expandable balloons in different lengths from each other and different locations from the distal end 116 of the catheter 102, such as in FIGS. 18A-18C.

The expandable members or balloons may be made of any biocompatible material which can expand upon activation from a fluid source such as air or water. The expandable member may have an inflation diameter of 0.5 cm to about 5.0 cm with the catheter shaft having an external diameter in a range between 5 and 9 french with a total length of at least 50 cm but could be as long as 90 cm. In other embodiments the expandable member or balloon has an inflation diameter of about 0.5 cm to about 2.5 cm. The shape of the expandable member or balloon may be circular, oval, tubular, rectangular, square, toroid, or any other geometric shape. The shape of the expandable member or balloon may be of a longer length than width such as a tube, oval or rectangular shape or could be more symmetrical such as in a circular shape. Any shape may be employed which is configured to guide if a guide member or to isolate if an isolating balloon or to occlude if an occlusion expandable member or balloon. The expandable member may be made of materials such as polymers, rubber, polyesters, nylons, Pebax, PET, polyurethanes, silicones or any expandable material. The number of expandable members or balloons may be anywhere from one to ten. In another embodiment the number of balloons is five. In yet another embodiment the number of balloons is four. Any combination of balloons as expandable members may be employed from one to ten or more expandable members such as balloons.

The guiding member, in this embodiment an expandable member or balloon 105 may have a diameter of about 0.5-1.0 cm as it is not configured to occlude blood flow but is used to guide the catheter shaft 102 through the aorta while reducing migration into the visceral arteries such as the inferior mesenteric artery 52, the superior mesenteric and renal arteries 50, and/or the celiac artery 48, as well as other smaller arteries or veins or other body openings. Less migration results in less wasted time and given the trauma and bleeding of the patient, every second counts. In other embodiments the guiding member if a balloon 105 may be configured to expand partially for guiding the distal end of the catheter at one point of the surgical procedure but then expanded further and configured to occlude or block flow of blood, such that the diameter could be from about 0.5 cm to about 3.0 cm.

The proximal end of the catheter device 100 is provided with a multi-port adapter 106. In this embodiment, the adapter 106 has five ports 108A, 108B, 108C, 108D, 111 and a main access port 110 which is an open port at the proximal end. The first port 108A is in fluid communication with the first balloon 104A. The second port 108B is in fluid communication with the second balloon 104B. The third port 108C is in fluid communication with the third balloon 104C. The fourth port 108D is in fluid communication with the fourth balloon 104D. The fifth port 111 is in fluid communication with the distal end guide balloon 105. The main access port 110 is in fluid communication with a distal port 116 on the distal end of the catheter shaft 102. The multi-port adapter 106 may also be an inflation port system such as shown in FIGS. 7-10 or FIG. 11. In these other embodiments the multi-port adapter or inflation port system 106 may be in the form of a hand trigger system such as shown in FIG. 2, or as a twist turn system as shown in FIGS. 15A-18C, though other manual or electronic systems may be employed which function to inflate and deflate the expandable members or balloons such as stockcock systems.

As shown in FIG. 2B, the hollow elongated catheter shaft 102 has a main inner lumen 112 and five inflation lumens 114A, 114B, 114C, 114D, 115. The main lumen 112 extends in fluid communication between the main access port 110 and the distal port 116. The first inflation lumen 114A extends in fluid communication between the first port 108A and the first balloon 104A. The second inflation lumen 114B extends in fluid communication between the second port 108B and the second balloon 104B. The third inflation lumen 114C extends in fluid communication between the third port 108C and the third balloon 104C. The fourth inflation lumen 114D extends in fluid communication between the fourth port 108D and the fourth balloon 104D. The fifth inflation lumen 115 extends in fluid communication between the fifth port 111 and the fifth guide balloon 105. The five inflation lumens 114A, 114B, 114C, 1140, 115 allow for independent inflation and deflation of the five balloons 104A, 104B, 104C, 1040, 105 by pumping a fluid (such as a saline solution or air or other medium) into and from the balloons via the ports 108A, 108B, 108C, 1080, 111, respectively.

The main lumen 112 and the distal port 116 may be used to pass a wide variety of surgical devices (such as guide wires, angioscopes, irrigation lines, aortic grafts and the like) into the aorta of the patient. While not shown in this embodiment but shown in other embodiments, a guide wire can be inserted into the main lumen 112 and extend out of the distal port 116 though one of the advantages of this embodiment of the present invention is the lack of a guide wire to guide the expandable members 104 into the aorta to the target location and instead there is an expandable member or balloon as the guiding member. The catheter shaft 102 may also include an additional port and lumen (not shown) that are in fluid communication with one another. The port and lumen are also in fluid communication with an aperture (not shown) in the catheter shaft. The aperture is disposed upstream with respect to the five balloons 104A, 104B, 104C, 104D, 105. These elements provide a manometer for measuring the upstream pressure within the aorta. A pressure monitor is attached the port to monitor the upstream pressure within the aorta.

The catheter shaft 102 preferably has an external diameter between 5 and 9 french such that it can be introduced into the left subclavian artery 20 (or possibly the left common carotid artery 18, the brachiocephalic trunk 16, the right common carotid artery 24, or the right subclavian artery 26) and advanced through the aortic arch 14 and down into the abdominal aorta 46. Alternatively, the catheter shaft 102 may be introduced into a femoral artery and advanced from below into the abdominal aorta 46. In this embodiment, the guide balloon 105 is located at the upmost distal end of the catheter shaft 102 in close proximity to the distal port 116. The guide balloon 105 is smaller in diameter than the other four balloons as the guide balloon reduces migration of the distal port into a visceral artery such as without limitation the inferior mesenteric artery 52, the superior mesenteric and renal arteries 50, and/or the celiac artery 48, as well as other smaller arteries or veins or other body openings. Such reduced migration lessens complications such as bleeding and importantly loss of time in treating the patient during a trauma or surgical procedure.

In this embodiment, the spacing of the four occluding balloons 104A, 104B, 104C, 104D along the distal portion of the catheter shaft 102 allows the balloons to be positioned in the abdominal aorta 46. This will generally require that the length of the catheter shaft 102 be at least 80 cm, and preferably about 90-100 cm. As described below in detail, the first balloon 104A (or the last balloon 104D) is inflated and located at the iliac bifurcation 40, and thus acts to fix the position of the catheter device 100 in the abdominal aorta 46. In this manner the first balloon 104A (or the last balloon 104D) secures the catheter device 100 and minimizes catheter movement within the abdominal aorta 46. The other balloons are inflated and/or deflated as desired in order to maintain pressure in the abdominal aorta 46 and thus stabilize the patient.

The catheter shaft 102 in each embodiment of the present invention may be formed of conventional polymers (e.g., polyethylene, polyvinyl chloride, PTFE, PEBAX and the like. The expandable members or balloons in each embodiment of the present invention may be formed of conventional polymer sheet material and the like as is well known in the art. The catheter shaft 102 and/or the occluding balloons 104A, 104B, 104C, 104D may incorporate radio-opaque material 101 to facilitate advancement and placement of the catheter utilizing fluoroscopic imaging techniques.

Figure 3:
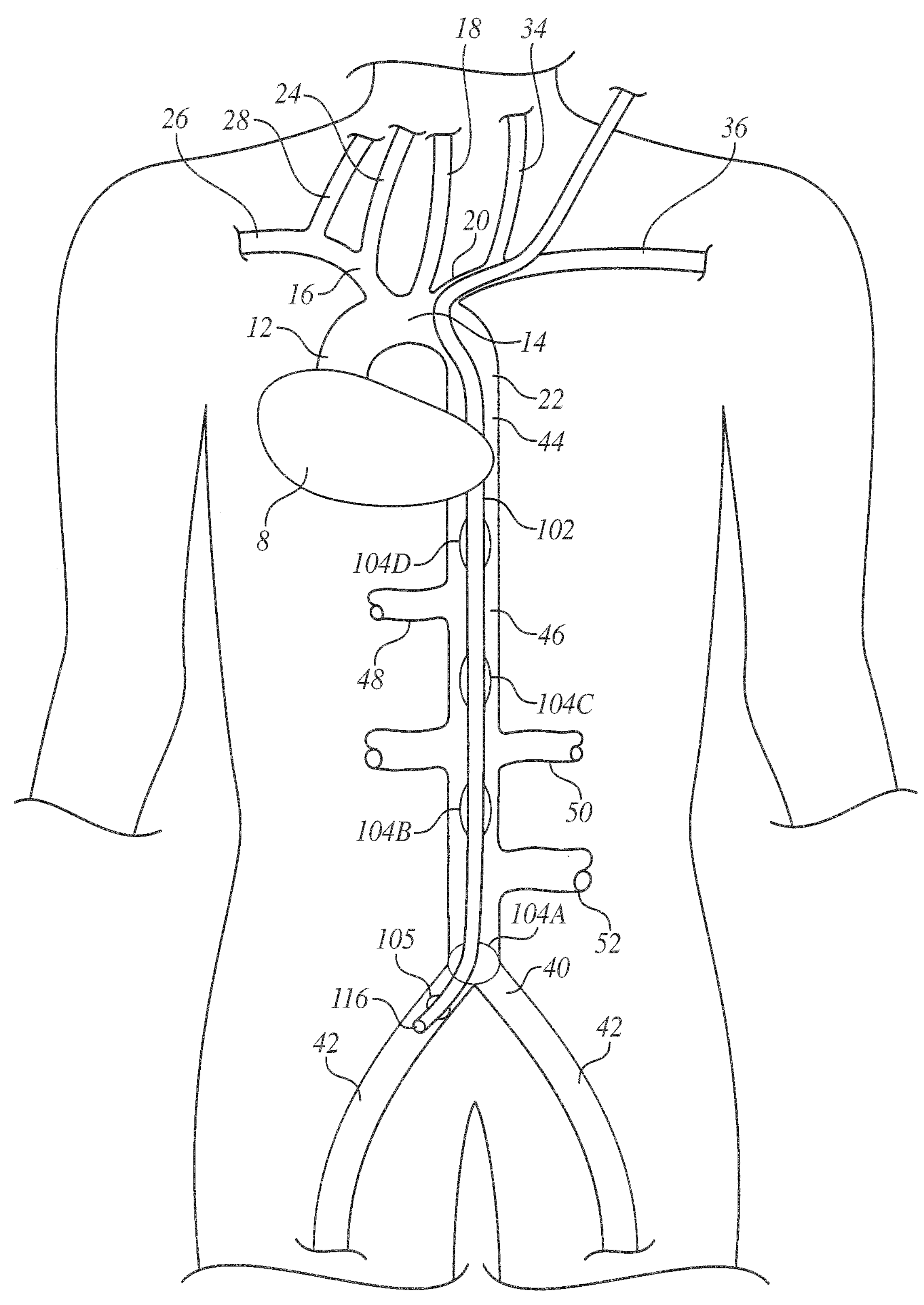
FIG. 3 is a schematic illustration showing the advancement and placement of the catheter device of FIG. 2A into the abdominal aorta via the subclavian artery during treatment for hemorrhagic shock in accordance with the present invention.

FIG. 3 illustrates the aortic catheter 100 with the four occluding balloons 104A, 104B, 104C, 104D disposed with the patient's abdominal aorta 46 and the guide balloon 105 within the iliac bifurcation 42. The catheter shaft 102 is introduced into the left subclavian artery 20 and advanced through the aortic arch 14 and down into the abdominal aorta 46. The guide balloon 105 is inflated (as shown) and then the catheter shaft 102 is moved distally such that the first balloon 104A is inflated and positioned at the iliac bifurcation 40. In this manner, the first balloon 104A, when inflated, fixes the position of the catheter device 100 in the abdominal aorta 46 and also occludes blood from flowing through the iliac bifurcation 42. As the guide balloon 105 is of a smaller diameter than the first occluding balloon 104, the guide balloon cannot functionally occlude blood. This configuration enables quick and efficient fixation of the aortic catheter device 100, which is advantageous in trauma situations where the patient is experiencing excessive internal bleeding.

After the catheter device 100 is fixed in position (e.g., with the first balloon 104A located at the iliac bifurcation 40), the other three balloons 104B, 104C, 104D are inflated and/or deflated as desired in order to identify and isolate a hemorrhage flowing from an artery in the abdominal aorta 46 and thus stabilize the patient.

More particularly, the second balloon 104B may be inflated to occlude blood from flowing downstream with respect to the balloon 104B. Because the second balloon 104B is positioned upstream from the inferior mesenteric artery 52, such occlusion blocks the flow of blood flowing through the inferior mesenteric artery 52. Similarly, the third balloon 104C may be inflated to occlude blood from flowing downstream with respect to the balloon 104C. Because the third balloon 104C is positioned upstream from the inferior mesenteric artery 52 and the superior mesenteric and renal arteries 50, such occlusion blocks the flow of blood flowing through the inferior mesenteric artery 52 as well as the superior mesenteric and renal arteries 50. Finally, the fourth balloon 104D may be inflated to occlude blood from flowing downstream with respect to the balloon 104D. Because the fourth balloon 104D is positioned upstream from the inferior mesenteric artery 52, the superior mesenteric and renal arteries 50 and the celiac artery 48, such occlusion blocks the flow of blood flowing through the inferior mesenteric artery 52, the superior mesenteric and renal arteries 50 as well as the celiac artery 48.

Note that when the fourth balloon 104D is pressurized to a level that does not occlude the flow of blood downstream therefrom, blood is pumped into the celiac artery 48 during systole. When the third and fourth balloons 104C, 104D are pressurized to a level that does not occlude the flow of blood downstream therefrom, blood is pumped into the celiac artery 48 and into the superior mesenteric and renal arteries 50 during systole. When the second, third and fourth occluding balloons 104B, 104C, 104D are pressurized to a level that does not occlude the flow of blood downstream therefrom, blood is pumped into the celiac artery 48, the superior mesenteric and renal arteries 50 and the inferior mesenteric artery 52 during systole. Finally, when the first, second, third and fourth occluding balloons 104A, 104B, 104C, 104D are pressurized to a level that does not occlude the flow of blood downstream therefrom, blood is pumped into the celiac artery 48, the superior mesenteric and renal arteries 50, the inferior mesenteric artery 52 and the iliac arteries 42 during systole.

As described above with respect to FIG. 3, the aortic catheter 100 of the present invention can be used to quickly identification and isolate a hemorrhage flowing from an artery in the abdominal aorta 46. Preferably, this is accomplished as follows: 1) introduce the catheter shaft into the left subclavian artery and inflate the guide balloon 105 and advance it through the aortic arch and down into the abdominal aorta, and then move the catheter device distally in order to locate the first balloon 104A at the iliac bifurcation 40 and inflate the first balloon; ii) if need be, adjust the inflation level of the first balloon 104A such that it blocks blood from flowing downstream through the iliac arteries; iii) monitor the aortic pressure at a position upstream from the four occluding balloons 104A, 104B, 104C, 104D; iv) if the pressure is normal (i.e., an indication that the hemorrhage has been isolated in the iliac arteries or one or more vessels downstream therefrom), end the manipulation of the occlusion of the four occluding balloons and continue monitoring the stability of the patient; surgical procedures are performed to identify and repair the injured artery, which typically requires opening up the abdominal cavity, locating the injured artery and then repairing the injured artery; v) if the pressure is low (i.e., an indication that the hemorrhage has not been isolated), adjust the inflation level of the fourth balloon 104D such that it blocks blood from flowing downstream therefrom; vi) monitor the aortic pressure at a position upstream from the four occluding balloons 104A, 104B, 104C, 104D; vii) if the pressure is low (i.e., an indication that the hemorrhage has not been isolated), it is probable that the source of the hemorrhage is upstream from the abdominal aorta 46 (e.g., within the thoracic aorta 44, the aortic arch 14, the ascending aorta 12 or vessels downstream therefrom); end the manipulation of the occlusion of the four balloons and continue monitoring the stability of the patient; surgical procedures are undertaken to identify and isolate the source of such bleeding utilizing other means. viii) if the pressure is normal, adjust the inflation level of the third balloon 104C such that it blocks blood from flowing downstream, and adjust the inflation level of the fourth balloon 104D such that it does not block blood from flowing downstream therefrom; this configuration allows blood to flow downstream into the celiac artery. ix) monitor the aortic pressure at a position upstream from the four occluding balloons 104A, 104B, 104C, 104D; x) if the pressure is low (i.e., an indication that the hemorrhage is flowing from the celiac artery), adjust the inflation level of the fourth balloon 104D such that it blocks blood from flowing downstream, thereby isolating the hemorrhage; end the manipulation of the occlusion of the four balloons and continue monitoring the stability of the patient; surgical procedures are performed to identify and repair the injured artery, which typically requires opening up the abdominal cavity, locating the injured artery and then repairing the injured artery; xi) if the pressure is normal, adjust the inflation level of the second balloon 104B such that it blocks blood from flowing downstream, and adjust the inflation levels of the fourth balloon 104D and third balloon 104C such that they do not block blood from flowing downstream, if need be; this configuration allows blood to flow downstream into the renal arteries and upper mesenteric artery. xii) monitor the aortic pressure at a position upstream from the four occluding balloons 104A, 104B, 104C, 104D; xiii) if the pressure is low (i.e., an indication that the hemorrhage is flowing from the renal arteries/upper mesenteric artery), adjust the inflation level of the third balloon 104C such that it blocks blood from flowing downstream, thereby isolating the hemorrhage; end the manipulation of the occlusion of the four balloons and continue monitoring the stability of the patient; surgical treatment is then performed to identify and repair the injured artery, which typically requires opening up the abdominal cavity, locating the injured artery and then repairing the injured artery; and xiv) if the pressure is normal (i.e., an indication that the hemorrhage is flowing from the lower mesenteric artery), the inflation level of the second balloon 104B is maintained such that it blocks blood from flowing downstream, thereby isolating the hemorrhage; end the manipulation of the occlusion of the four balloons and continue monitoring the stability of the patient; surgical treatment is then performed to identify and repair the injured artery, which typically requires opening up the abdominal cavity, locating the injured artery and then repairing the injured artery.

The sequence of operations set forth in i)-xiv) directly above advantageously provides timely hemostasis, which is typically suitable for critically injured patients. However, it blocks blood flow through the upper arteries of the abdominal cavity (e.g., the celiac and renal arteries), thereby potentially impacting the normal function of the organs (e.g., the liver and/or kidney) that rely on the upper arteries of the abdominal cavity. Thus, in some circumstances (for example, where the blood pressure of the patient is not in a critical condition), an alternate sequence of operations may be used. For example, the four occluding balloons 104B, 104C, 104D may be sequentially inflated/deflated in order to isolate the hemorrhage. This sequence of operations potentially minimizes the loss of blood flow through the upper arteries of the abdominal cavity (e.g., the celiac and renal arteries), and thus minimizes the potential impact to the normal function of the organs (e.g., the liver and/or kidney) that rely on the upper arteries of the abdominal cavity.

Figure 4:
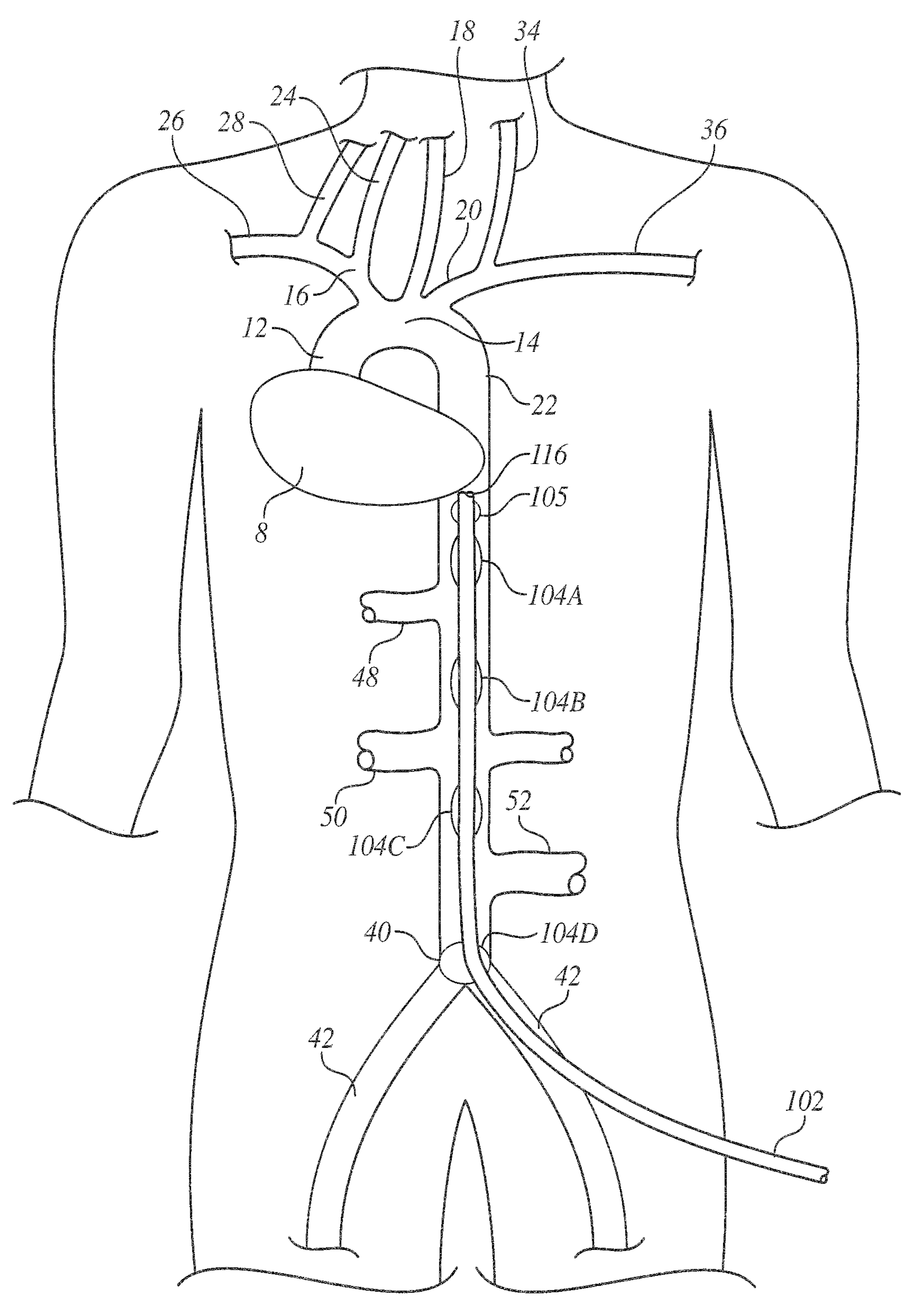
FIG. 4 is a schematic illustration showing the advancement and placement of the catheter device of FIG. 2A into the abdominal aorta via the femoral artery during treatment for hemorrhagic shock in accordance with the present invention.

FIG. 4 illustrates the aortic catheter 100 with the guide balloon 105 and four occluding balloons 104A, 104B, 104C, 104D disposed with the patient's abdominal aorta 46. The catheter shaft 102 is introduced into the femoral artery and advanced through the iliac bifurcation 40 such that the guide balloon 105 and four occluding balloons 104A, 104B, 104C, 104D are positioned in the abdominal aorta 46. The guide balloon 105 is inflated and then the catheter shaft 102 is moved proximally such that the fourth balloon 104D is positioned at the iliac bifurcation 40 as shown and inflated. In this manner, the fourth balloon 104D, when inflated, fixes the position of the catheter device 100 in the abdominal aorta 46 and also occludes blood from flowing through the iliac bifurcation. This configuration enables quick and efficient fixation of the aortic catheter device 100, which is advantageous in trauma situations where the patient is experiencing excessive internal bleeding.

After the catheter device 100 is fixed in position (e.g., with the fourth balloon 104D located at the iliac bifurcation 40), the other three occluding balloons 104A, 104B, 104C are inflated and/or deflated as desired in order to identify and isolate a hemorrhage flowing from an artery in the abdominal aorta 46 and thus stabilize the patient.

More particularly, the third balloon 104C may be inflated to occlude blood from flowing downstream with respect to the balloon 104C. Because the third balloon 104C is positioned upstream from the inferior mesenteric artery 52, such occlusion blocks the flow of blood flowing through the inferior mesenteric artery 52. Similarly, the second balloon 104B may be inflated to occlude blood from flowing downstream with respect to the balloon 104B. Because the second balloon 104B is positioned upstream from the inferior mesenteric artery 52 and the superior mesenteric and renal arteries 50, such occlusion blocks the flow of blood flowing through the inferior mesenteric artery 52 as well as the superior mesenteric and renal arteries 50. Finally, the first balloon 104A may be inflated to occlude blood from flowing downstream with respect to the balloon 104A. Because the first balloon 104A is positioned upstream from the inferior mesenteric artery 52, the superior mesenteric and renal arteries 50 and the celiac artery 48, such occlusion blocks the flow of blood flowing through the inferior mesenteric artery 52, the superior mesenteric and renal arteries 50 as well as the celiac artery 48.

Note that when the first balloon 104A is pressurized to a level that does not occlude the flow of blood downstream therefrom, blood is pumped into the celiac artery 48 during systole. When the first and second balloons 104A, 104B are pressurized to a level that does not occlude the flow of blood downstream therefrom, blood is pumped into the celiac artery 48 and into the superior mesenteric and renal arteries 50 during systole. When the first, second and third balloons 104A, 104B, 104C are pressurized to a level that does not occlude the flow of blood downstream therefrom, blood is pumped into the celiac artery 48, the superior mesenteric and renal arteries 50 and the inferior mesenteric artery 52 during systole. Finally, when the first, second, third and fourth occluding balloons 104A, 104B, 104C, 104D are pressurized to a level that does not occlude the flow of blood downstream therefrom, blood is pumped into the celiac artery 48, the superior mesenteric and renal arteries 50, the inferior mesenteric artery 52 and the iliac arteries 42 during systole.

As described above with respect to FIG. 4, the aortic catheter 100 of the present invention can be used to quickly identification and isolate a hemorrhage flowing from an artery in the abdominal aorta 46. Preferably, this is accomplished as follows: i) introduce the catheter shaft into the renal artery and inflate the guide balloon 105 and then advance it up into the abdominal aorta, and move the catheter device proximally in order to locate the fourth balloon 104D at the iliac bifurcation 40 and inflate the fourth balloon 104D; ii) if need be, adjust the inflation level of the fourth balloon 104D such that it blocks blood from flowing downstream through the iliac arteries; iii) monitor the aortic pressure at a position upstream from the four occluding balloons 104A, 104B, 104C, 104D; iv) if the pressure is normal (i.e., an indication that the hemorrhage has been isolated in the iliac arteries or one or more vessels downstream therefrom), end the manipulation of the occlusion of the four balloons and continue monitoring the stability of the patient; surgical procedures are performed to identify and repair the injured artery, which typically requires opening up the abdominal cavity, locating the injured artery and then repairing the injured artery; v) if the pressure is low (i.e., an indication that the hemorrhage has not been isolated), adjust the inflation level of the first balloon 104A such that it blocks blood from flowing downstream therefrom; vi) monitor the aortic pressure at a position upstream from the four occluding balloons 104A, 104B, 104C, 104D; vii) if the pressure is low (i.e., an indication that the hemorrhage has not been isolated), it is probable that the source of the hemorrhage is upstream from the abdominal aorta 46 (e.g., within the thoracic aorta 44, the aortic arch 14, the ascending aorta 12 or vessels downstream therefrom); end the manipulation of the occlusion of the four balloons and continue monitoring the stability of the patient; surgical procedures are undertaken to identify and isolate the source of such bleeding utilizing other means; viii) if the pressure is normal, adjust the inflation level of the second balloon 104B such that it blocks blood from flowing downstream, and adjust the inflation level of the first balloon 104A such that it does not block blood from flowing downstream therefrom; this configuration allows blood to flow downstream into the celiac artery. ix) monitor the aortic pressure at a position upstream from the four occluding balloons 104A, 104B, 104C, 104D; x) if the pressure is low (i.e., an indication that the hemorrhage is flowing from the celiac artery), adjust the inflation level of the first balloon 104A such that it blocks blood from flowing downstream, thereby isolating the hemorrhage; end the manipulation of the occlusion of the four balloons and continue monitoring the stability of the patient; surgical procedures are performed to identify and repair the injured artery, which typically requires opening up the abdominal cavity, locating the injured artery and then repairing the injured artery; xi) if the pressure is normal, adjust the inflation level of the third balloon 104C such that it blocks blood from flowing downstream, and adjust the inflation levels of the first balloon 104A and second balloon 104B such that they do not block blood from flowing downstream, if need be; this configuration allows blood to flow downstream into the renal arteries and upper mesenteric artery. xii) monitor the aortic pressure at a position upstream from the four occluding balloons 104A, 104B, 104C, 104D; xiii) if the pressure is low (i.e., an indication that the hemorrhage is flowing from the renal arteries/upper mesenteric artery), adjust the inflation level of the second balloon 1043 such that it blocks blood from flowing downstream, thereby isolating the hemorrhage; end the manipulation of the occlusion of the four balloons and continue monitoring the stability of the patient; surgical treatment is then performed to identify and repair the injured artery, which typically requires opening up the abdominal cavity, locating the injured artery and then repairing the injured artery; and xiv) if the pressure is normal (i.e., an indication that the hemorrhage is flowing from the lower mesenteric artery), the inflation level of the third balloon 104C is maintained such that it blocks blood from flowing downstream, thereby isolating the hemorrhage; end the manipulation of the occlusion of the four balloons and continue monitoring the stability of the patient; surgical treatment is then performed to identify and repair the injured artery, which typically requires opening up the abdominal cavity, locating the injured artery and then repairing the injured artery.

The sequence of operations set forth in i)-xiv) directly above advantageously provides timely hemostasis, which is typically suitable for critically injured patients. However, it blocks blood flow through the upper arteries of the abdominal cavity (e.g., the celiac and renal arteries), thereby potentially impacting the normal function of the organs (e.g., the liver and/or kidney) that rely on the upper arteries of the abdominal cavity. Thus, in some circumstances (for example, where the blood pressure of the patient is not in a critical condition), an alternate sequence of operations may be used. For example, the balloons 104C, 104B, 104A may be sequentially inflated/deflated in order to isolate the hemorrhage. This sequence of operations potentially minimizes the loss of blood flow through the upper arteries of the abdominal cavity (e.g., the celiac and renal arteries), and thus minimizes the potential impact to the normal function of the organs (e.g., the liver and/or kidney) that rely on the upper arteries of the abdominal cavity.

Advantageously, the aortic occlusion device 100 of the present invention can be fixated within the abdominal aorta and manipulated in order to quickly and efficiently identify and isolate a hemorrhage flowing from an artery in the abdominal aorta, and thus stabilize the patient. Such operations are beneficial in trauma situations where the patient is experiencing excessive internal bleeding and quick stabilization provides time for interventional treatment. The guide balloon 105 reduces the time until occlusion as it reduces the migration of the catheter 102 into arteries and other vasculature.

Figure 5:
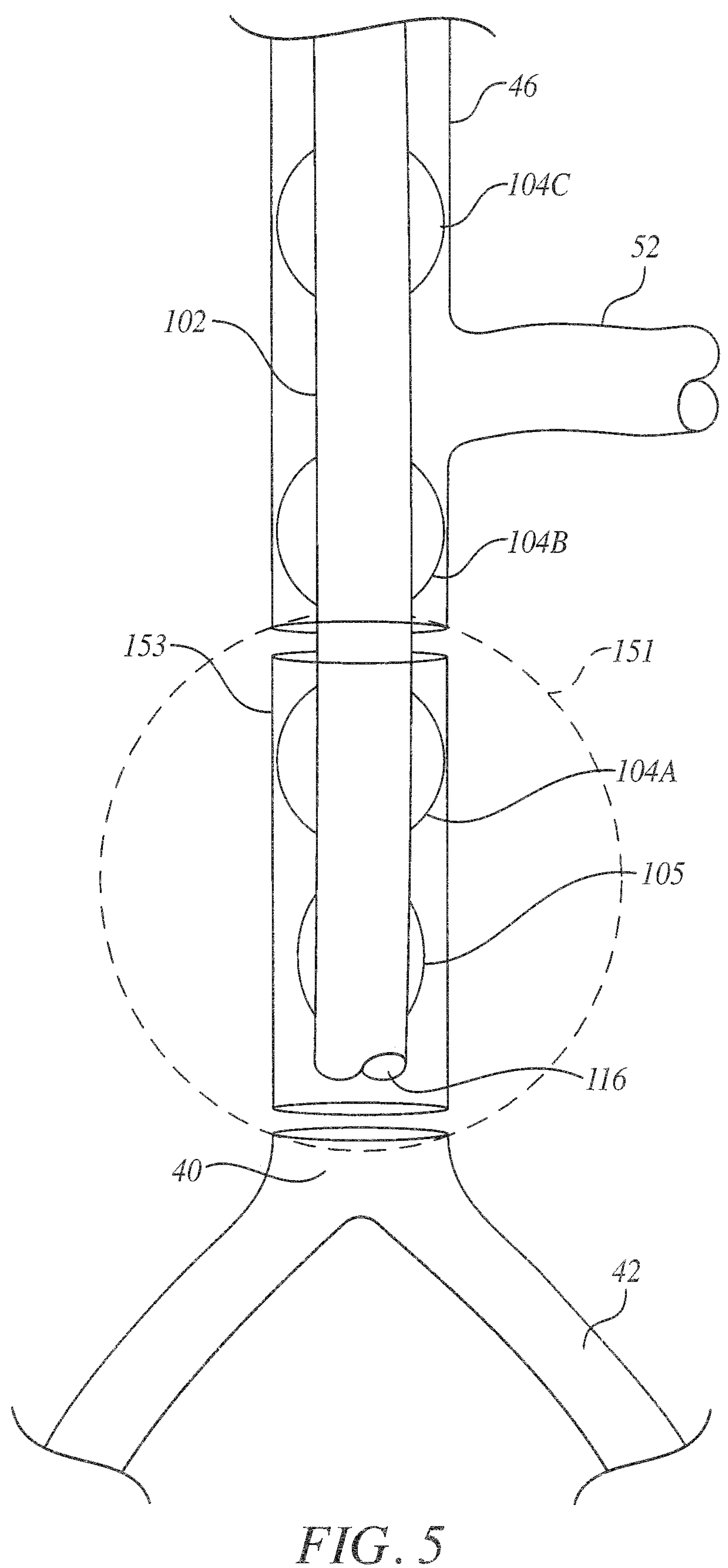
FIG. 5 is a schematic illustration showing the placement of the catheter device of FIG. 2A into the abdominal aorta during open surgery of an abdominal aortic aneurysm in accordance with the present invention.

In another aspect of the present invention, the aortic occlusion device 100 can be used in treating an abdominal aortic aneurysm, which is an abnormal ballooning of the abdominal aorta. In such applications, the distal portion of the aortic catheter 100 (with the balloons 104A, 1048, 104C, 104D, 105) is located with the patient's abdominal aorta 46. It may be introduced from above (e.g., into and through the subclavian artery or other artery extending from the aortic arch) as shown in FIG. 5, or introduced from below (e.g., into and through the femoral artery), and advanced into the abdominal aorta as described above. An incision is made into the abdominal cavity and the aneurysm 151 is exposed. The guide balloon 105 is inflated as well as one or more of the occlusion balloons of the device 100, which are located upstream from the aneurysm 151, are inflated to a level that occludes the flow of blood downstream, thereby effectively clamping the section of the abdominal aorta 46 that is upstream from the aneurysm 151. The aneurysm 151 is opened and a graft 153 is inserted to bridge the normal aorta above the aneurysm to the normal aorta below the aneurysm. Alternatively, a bifurcated graft may be used to bridge the aorta 46 to the iliac arteries 42. The lumbar arteries may be clamped to prevent back bleeding. A portion of the catheter shaft 102 together with one or more of the occlusion balloons may be disposed within the aneurysm (for example, the part of the catheter shaft supporting guide balloon 105 and first occluding balloon 104A as shown in FIG. 5). In this case, before the graft 153 is affixed to the aorta, it may be placed around the outer diameter of that part of the catheter shaft that extends into the aneurysm 151, and the inflatable balloon disposed within the graft 153, if any, may be inflated to temporarily hold the graft 153 in place. In such applications, the four independently inflatable occluding balloons 104A, 104B, 104C, 104D advantageously provide flexibility in occluding various parts of the abdominal aorta 46. Moreover, the quick and efficient fixation of the catheter device 100 within the abdominal aorta can potentially provide time savings during surgery.

Figure 6:
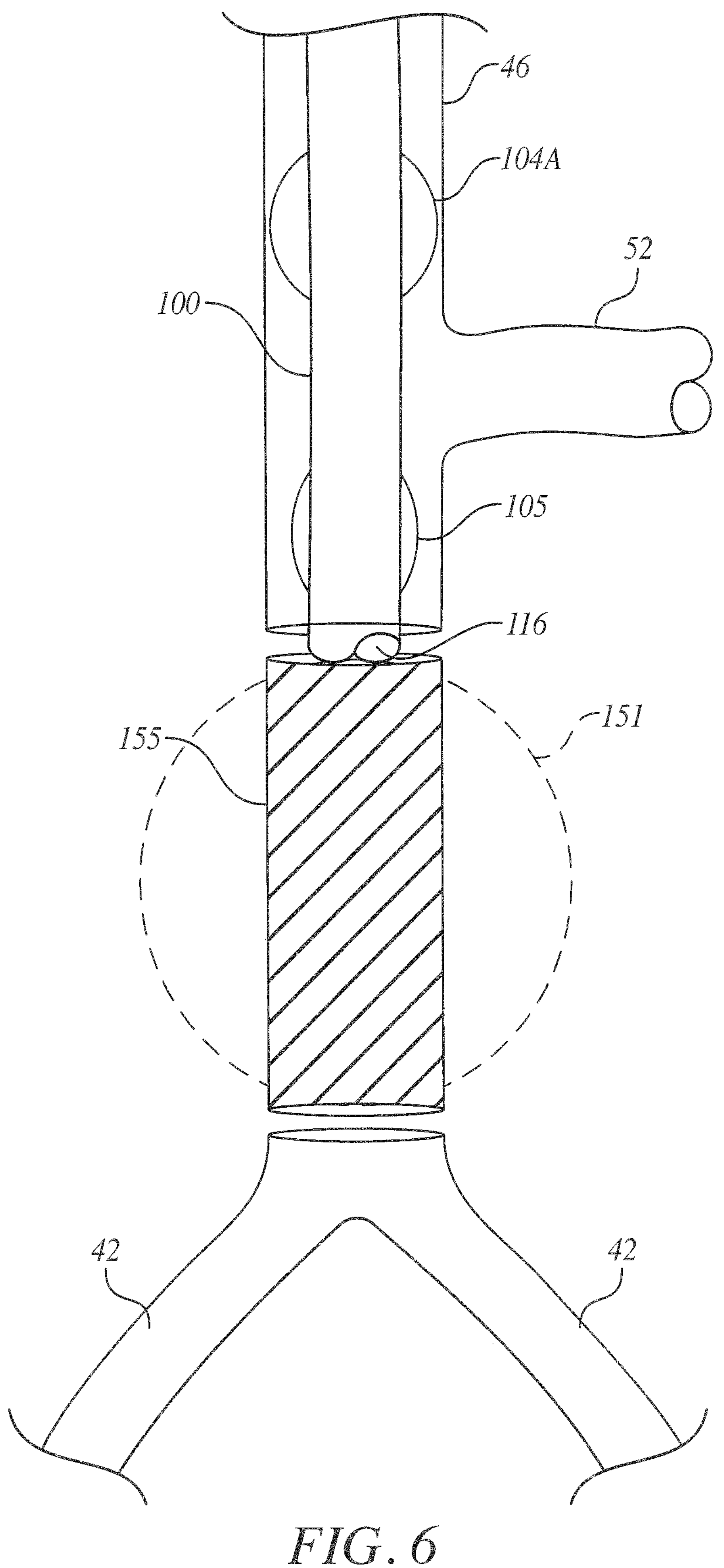
FIG. 6 is a schematic illustration showing the placement of the catheter device of FIG. 2A into the abdominal aorta during catheter-based surgery of an abdominal aortic aneurysm in accordance with the present invention.

In yet another aspect of the invention, the aortic occlusion device 100 can be used in a catheter-based treatment of an abdominal aortic aneurysm whereby a stent-graft is seated in the normal aorta above and below the aneurysm, thereby effectively isolating the aneurysm sac from the circulation. In this technique, the stent-graft provides a new normal-sized lumen to maintain blood flow. In such applications, the aortic catheter 100 (with the balloons 104A, 104B, 104C, 104D, 105) is located with the patient's abdominal aorta 46. It may be introduced from above (e.g., into and through the subclavian artery or other artery extending from the aortic arch) as shown in FIG. 6, or introduced from below (e.g., into and through the femoral artery), and advanced into the abdominal aorta as described above. Fluoroscopic imaging techniques are preferably used to locate the distal port 116 of the catheter shaft 102 at the desired position adjacent the aneurysm 151. One or more of the occlusion balloons of the catheter device 100 (e.g., such as the first occlusion balloon 104A as shown) may be inflated to a level that occludes the flow of blood, thereby effectively clamping the abdominal aorta section. The stent-graft 155 is then deployed through the distal port 116 of the catheter device 100, and the catheter device 100 is removed. In such applications, the four independently inflatable occluding balloons 104A, 104B, 104C, 104D advantageously provide flexibility in occluding various parts of the abdominal aorta 46. Moreover, the quick and efficient fixation of the catheter device 100 within the abdominal aorta 46 can potentially provide time savings during surgery.

Figure 7:
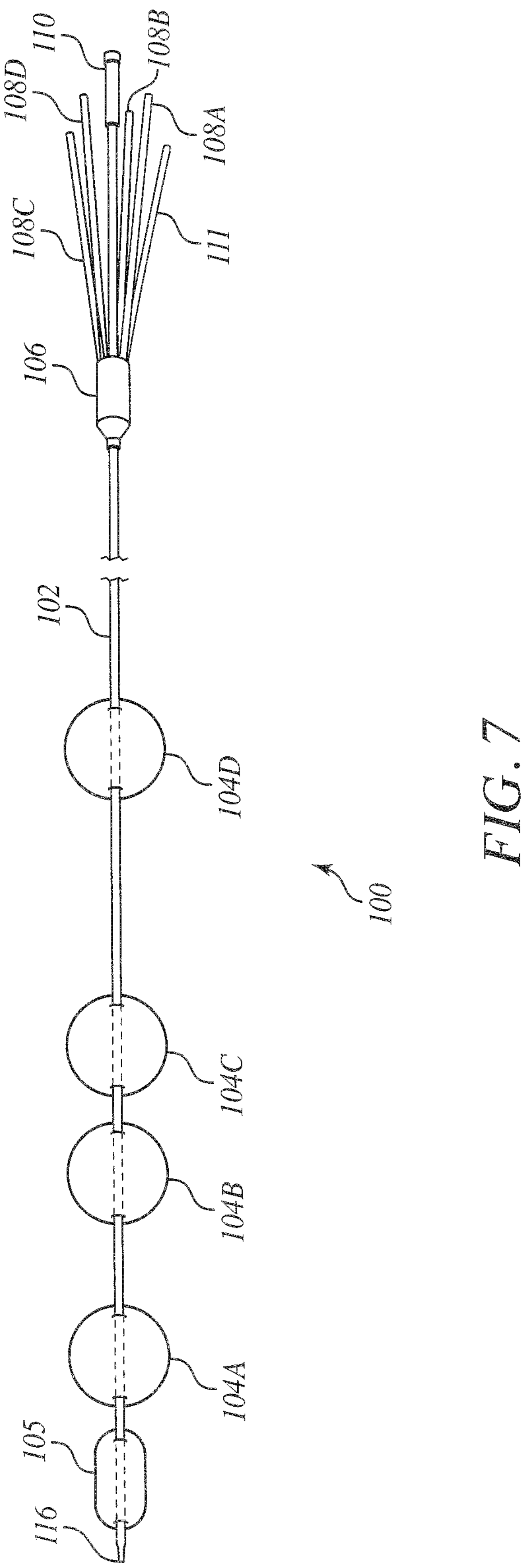
FIG. 7 is a side view of an illustrative embodiment of another embodiment of a catheter device in accordance with the present invention including five expandable members with another embodiment of the inflation ports on the proximal end of the catheter device.

FIG. 7 shows another view of the inventive catheter device including a guide balloon 105 and four occluding balloons 104A, 104B, 104C, 104D. FIG. 7 also shows an alternate inflation port system 106, 108A, 108B, 108C, 108D, 111. There are five balloons 104A, 104B, 104C, 104D, 105 shown in FIG. 7 in the inflated state with the smaller diameter of the guide balloon 105 seen relative to the diameter of the four occluding balloons 104A, 104B, 104C, 104D. Other diameter sizes may be employed including the guide balloon 105 the same diameter size as the other expandable member balloons, or a different geometrical shape as the other expandable member balloons or where the guide member or balloon is a larger diameter size compared to the other expandable member balloons.

Figures 8A, 8B, 8C:
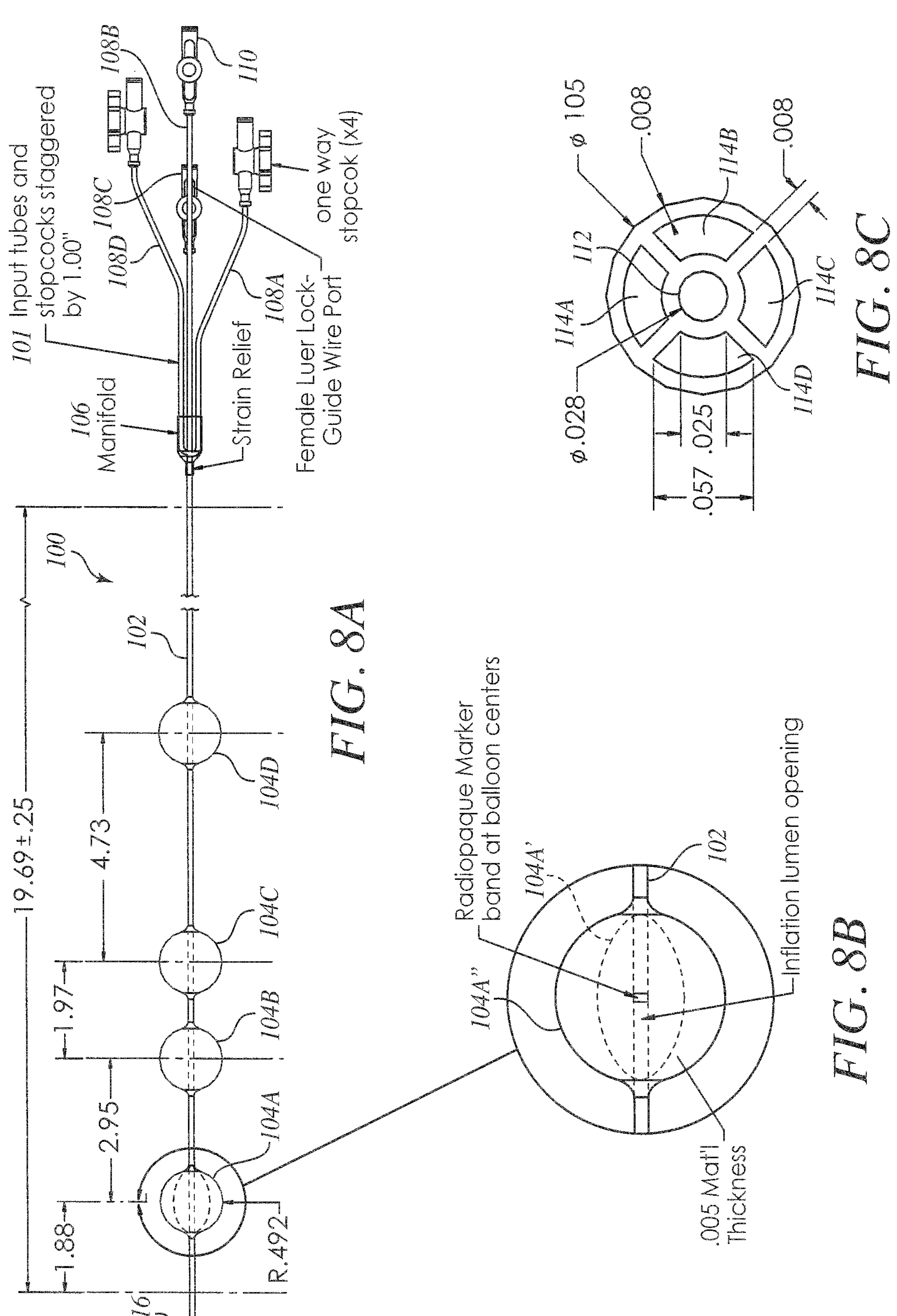
FIGS. 8A-8C are another embodiment of the present invention with 8A a side view and an exploded view of the distal end expandable member of another embodiment of a catheter device in accordance with the present invention including four expandable members wherein the distal end expandable member has two inflation states with one inflation state half-way inflated and the second inflation state in full inflation.
Figure 9A:
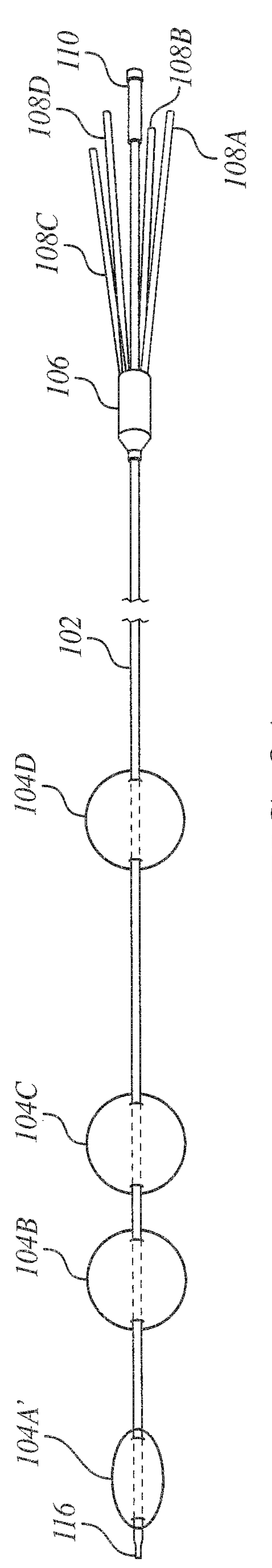
Figure 9B:
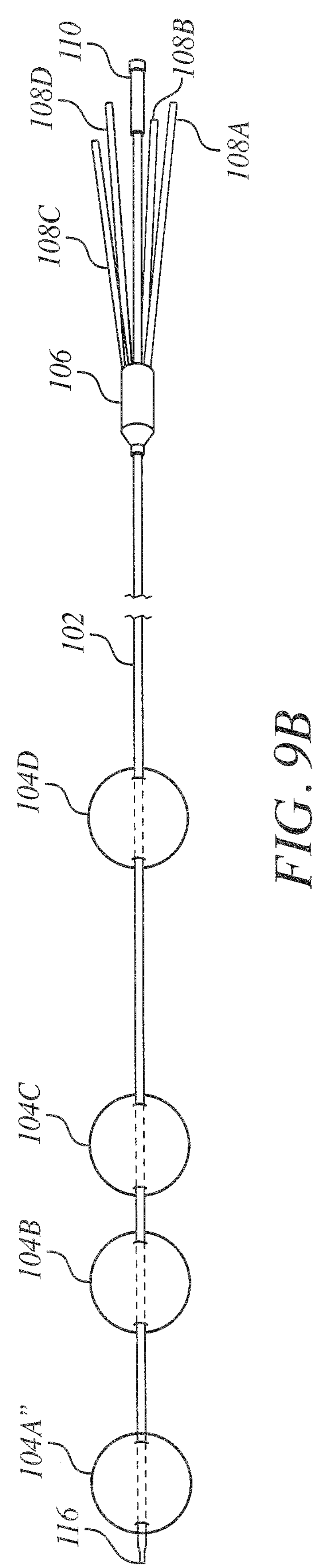

FIGS. 8A-8C and 9A-9B show another embodiment of the present invention wherein the first occluding balloon 104A has two inflation states so that it may be used as the guide balloon. As shown in FIGS. 8A and 8B by the dotted lines 104A', the first balloon 104A may be inflated half-way, for instance to a diameter of about 0.5-1.0 cm, as shown in the first inflation state as 104A' and therefore is configured to be a guide balloon. The second inflation state 104" is when the first balloon 104 is fully inflated, for instance to a diameter of about 2.5-3.0 cm, as shown 104" and therefore configured to be an occluding balloon at that time. In this embodiment there are only four balloons 104A. 104B. 104C, 104D with the first balloon 104A having a first inflation state 104A' functioning as a guide balloon and a second inflation state 104A" functioning as an occluding balloon. As shown in FIG. 9A, the first balloon 104 is inflated half-way into the first inflation state 104A' and serves as a guide balloon. As shown in FIG. 9B, the first balloon 104 is inflated fully into the second inflation state 104A" and serves as an occluding balloon Thus the first balloon 104A may act as both the guide balloon and an occluding balloon. The methodology as shown above wherein the first balloon may be inflated to the second inflation state 104K" so as to occlude the celiac artery 48 or the iliac bifurcation 42 depending on whether the inventive catheter device 100 is initial inserted in the subclavian artery or femoral artery, may be employed using this embodiment.

Figure 10:
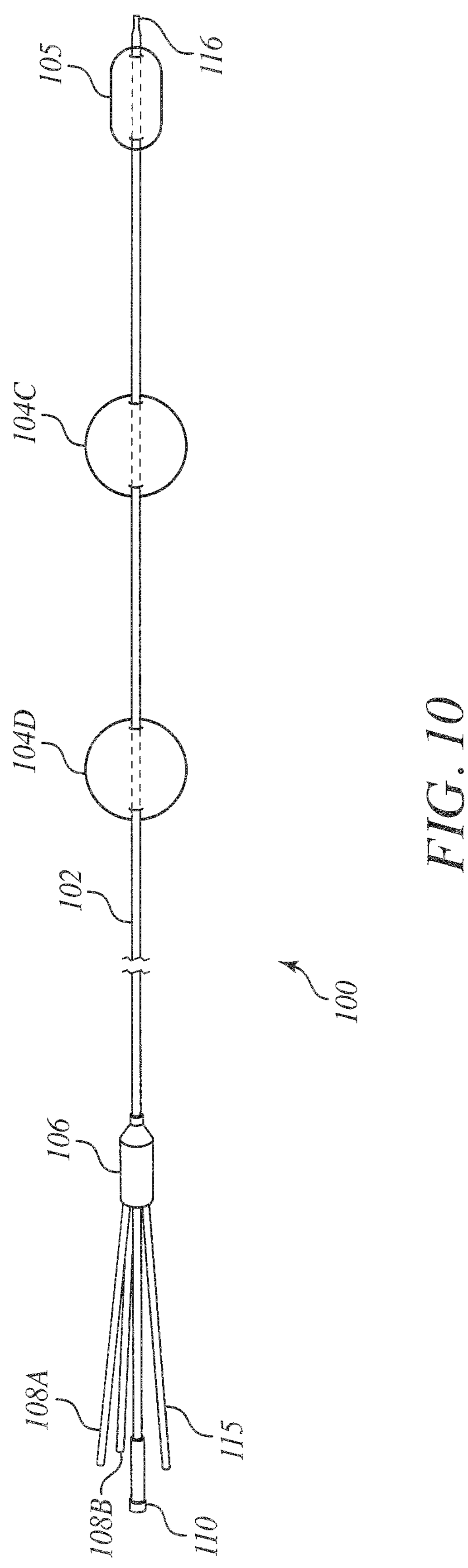
FIG. 10 is a side view of another embodiment of a catheter device in accordance with the present invention including three expandable members.
Figure 11A:
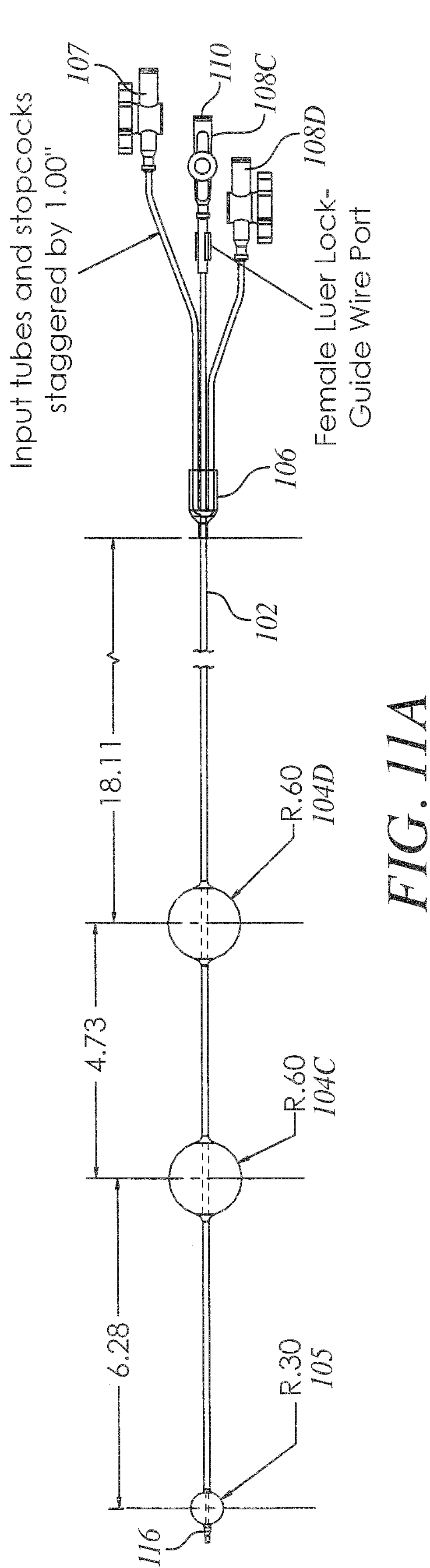
Figure 11B:
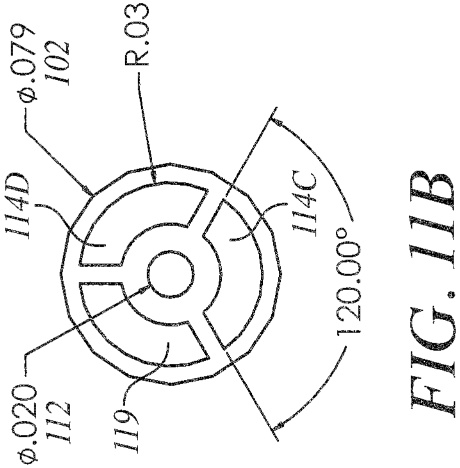

FIGS. 10 and 11 show yet another embodiment of the present invention including the guide balloon 105 and two occluding balloons 104C, 104D spaced the same distance from the distal end port 116 as in the previous embodiments. In this embodiment the spacing between occluding balloons 104C, 104D is regular at a distance of approximately 10 cm though other distances could be employed in the range of about 5 cm to about 30 cm distance from one another along the catheter 102. In this configuration, there is a distance on the order of approximately 20-30 cm between the guide balloon 105 and the proximal balloon 104D. These dimensions correspond to the configuration and spacing of the major arteries (e.g., the celiac artery 48, renal arteries and superior mesenteric artery 50, inferior mesenteric artery 52, iliac bifurcation 40) of the abdominal aorta 46 as described above in the methodology having either five balloons (guide balloon 105 and four occluding balloons 104A, 104B, 104C, 104D of FIGS. 2A-8) or four balloons (FIGS. 9-10B). In other embodiments that distance between the guide balloon 105 and the proximal balloon 104D could be in the range of about 20 cm to about 60 cm.

By way of example employing the embodiment of three total balloons 105, 104C, 104D as shown in FIGS. 10-11, the medical professional would: i) introduce the catheter shaft 102 into the left subclavian artery and then inflate the guide balloon 105 and advance it through the aortic arch and down into the abdominal aorta, and move the catheter device distally in order to locate the balloon 104C at one of the visceral arteries such as the iliac bifurcation 40, celiac artery 48, the superior mesenteric and renal arteries 50, and the inferior mesenteric artery 52, and inflate balloon 104C to occlude the target artery; ii) if need be, adjust the inflation level of the occluding balloon 104C such that it blocks blood from flowing downstream through the target arteries; iii) monitor the aortic pressure at a position upstream from the two occluding balloons 104C, 104D; iv) if the pressure is normal (i.e., an indication that the hemorrhage has been isolated in the iliac arteries or one or more vessels downstream therefrom), end the manipulation of the occlusion of the two occluding balloons 104C, 104D, and continue monitoring the stability of the patient; surgical procedures are performed to identify and repair the injured artery, which typically requires opening up the abdominal cavity, locating the injured artery and then repairing the injured artery; v) if the pressure is low (i.e., an indication that the hemorrhage has not been isolated), adjust the inflation level of the occluding balloon 104D such that it blocks blood from flowing downstream therefrom; vi) monitor the aortic pressure at a position upstream from the two occluding balloons 104C, 104D; vii) if the pressure is low (i.e., an indication that the hemorrhage has not been isolated), it is probable that the source of the hemorrhage is upstream from the abdominal aorta 46 (e.g., within the thoracic aorta 44, the aortic arch 14, the ascending aorta 12 or vessels downstream therefrom); end the manipulation of the occlusion of the two occluding balloons and continue monitoring the stability of the patient; surgical procedures are undertaken to identify and isolate the source of such bleeding utilizing other means. viii) if the pressure is normal, adjust the inflation level of the occluding balloon 104C such that it blocks blood from flowing downstream, and adjust the inflation level of the occluding balloon 104D such that it does not block blood from flowing downstream therefrom; this configuration allows blood to flow downstream into the celiac artery. ix) monitor the aortic pressure at a position upstream from the two occluding balloons 104C, 104D; x) if the pressure is low (i.e., an indication that the hemorrhage is flowing from the celiac artery), adjust the inflation level of the last occluding balloon 1040 such that it blocks blood from flowing downstream, thereby isolating the hemorrhage; end the manipulation of the occlusion of the two occluding balloons and continue monitoring the stability of the patient; surgical procedures are performed to identify and repair the injured artery, which typically requires opening up the abdominal cavity, locating the injured artery qand then repairing the injured artery; xi) if the pressure is normal, adjust the inflation levels of the two occluding balloons 104C 104D such that one or both or neither blocks blood from flowing downstream, if need be; this configuration allows blood to flow downstream into the renal arteries and upper mesenteric artery. xii) monitor the aortic pressure at a position upstream from the two occluding balloons 104C, 104D; xiii) if the pressure is low (i.e., an indication that the hemorrhage is flowing from the renal arteries/upper mesenteric artery), adjust the inflation level of the balloon 104C such that it blocks blood from flowing downstream, thereby isolating the hemorrhage; end the manipulation of the occlusion of the two occluding balloons and continue monitoring the stability of the patient; surgical treatment is then performed to identify and repair the injured artery, which typically requires opening up the abdominal cavity, locating the injured artery and then repairing the injured artery; and xiv) if the pressure is normal (i.e., an indication that the hemorrhage is flowing from the lower mesenteric artery), the inflation level of the occluding balloon 104C is maintained such that it blocks blood from flowing downstream, thereby isolating the hemorrhage; end the manipulation of the occlusion of the two occluding balloons and continue monitoring the stability of the patient; surgical treatment is then performed to identify and repair the injured artery, which typically requires opening up the abdominal cavity, locating the injured artery and then repairing the injured artery.

The sequence of operations set forth in i)-xiv) directly above advantageously provides timely hemostasis, which is typically suitable for critically injured patients. However, it blocks blood flow through the upper arteries of the abdominal cavity (e.g., the celiac and renal arteries), thereby potentially impacting the normal function of the organs (e.g., the liver and/or kidney) that rely on the upper arteries of the abdominal cavity. Thus, in some circumstances (for example, where the blood pressure of the patient is not in a critical condition), an alternate sequence of operations may be used. For example, the two occluding balloons 104C, 104D may be sequentially inflated/deflated in order to isolate the hemorrhage. This sequence of operations potentially minimizes the loss of blood flow through the upper arteries of the abdominal cavity (e.g., the celiac and renal arteries), and thus minimizes the potential impact to the normal function of the organs (e.g., the liver and/or kidney) that rely on the upper arteries of the abdominal cavity. The guide balloon 105 acts as a guide for the catheter device 100 within the aorta and reduces migration, complications, bleeding and time in treating the patient.

In another example, the embodiment of FIGS. 11-12 having three total balloons being the guide balloon 105 and two occluding balloons 104C, 104D may be employed by introducing the catheter shaft 102 into the femoral artery and advancing through the iliac bifurcation 40 such that the guide balloon 105 and two occluding balloons 104C, 104D are positioned in the abdominal aorta 46. The guide balloon 105 is inflated and then the catheter shaft 102 is moved proximally such that the last occluding balloon 104D is positioned at the iliac bifurcation 40 as shown and inflated. In this manner, the last occluding balloon 104D, when inflated, fixes the position of the catheter device 100 in the abdominal aorta 46 and also occludes blood from flowing through the iliac bifurcation. This configuration enables quick and efficient fixation of the aortic catheter device 100, which is advantageous in trauma situations where the patient is experiencing excessive internal bleeding. A similar methodology as above i)-xiv) or the reverse depending on insertion point in the body is employed to control blow flow to the various arteries such as the celiac artery 48, the superior mesenteric and renal arteries 50, and the inferior mesenteric artery 52, and inflate balloon 104C to occlude the target artery, by varying inflation of the two occluding balloons 104C, 104D to either stop blood flow or allow a controlled amount of blood flow around the occluding balloon 104C, 104D when in a non-inflated state.

Figure 12A:
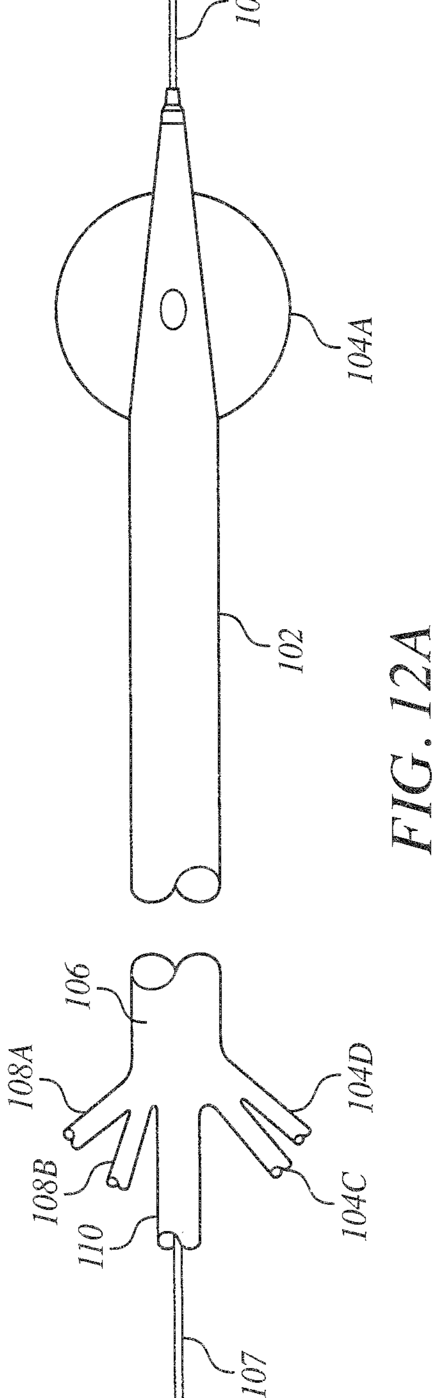
FIGS. 12A and 12B are side views of another embodiment of a catheter device in accordance with the present invention including a memory shape wire which is just outside of the lumen distal end in FIG. 12A and is in the activated state outside the lumen distal end in FIG. 12B.
Figure 12B:
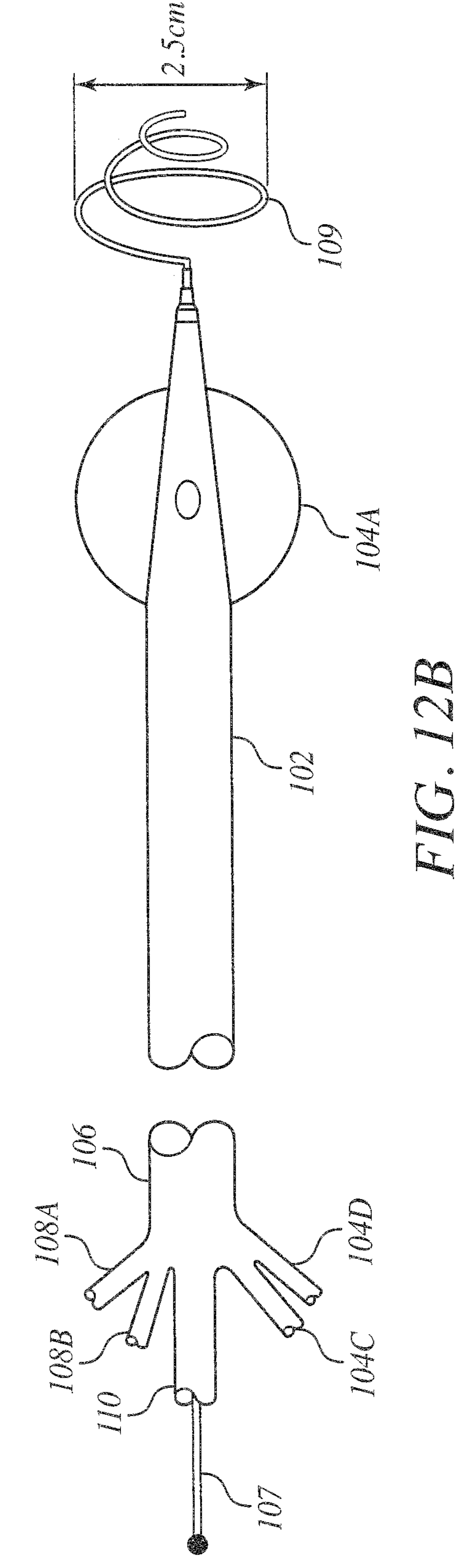
Figure 13:
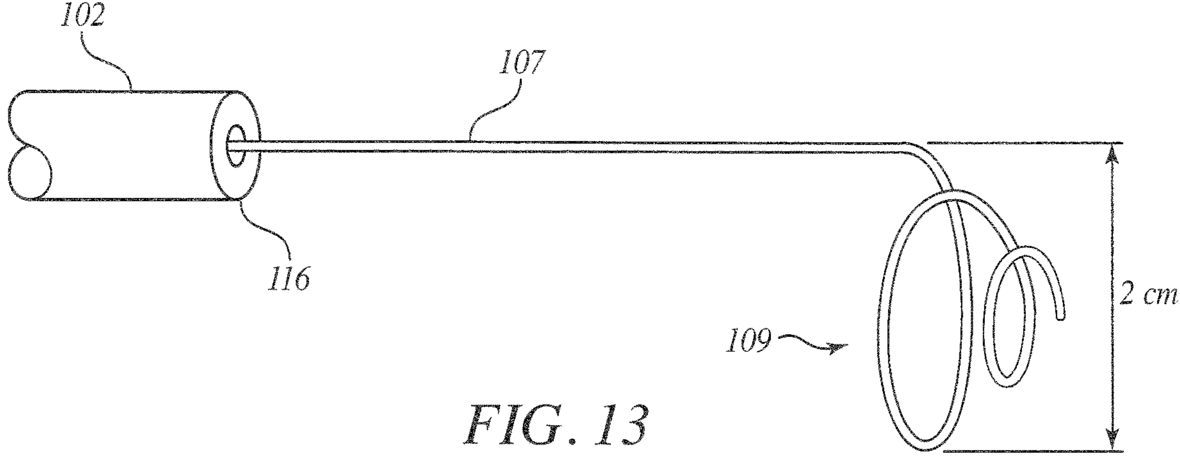
FIG. 13 is an exploded view of the activated distal end of the memory shape wire of FIG. 12B.
Figure 14A:
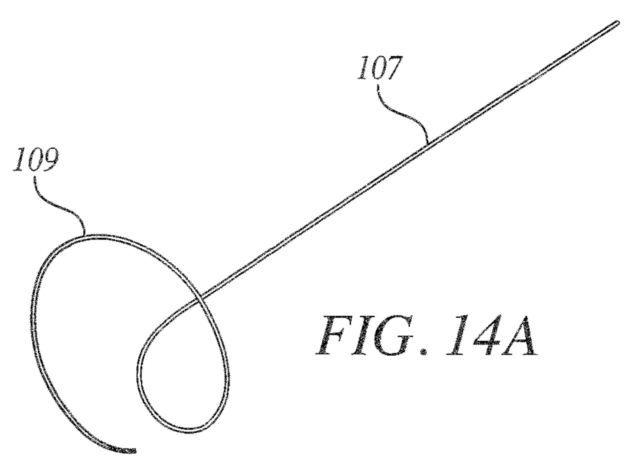
FIGS. 14A and 14B show two possible shapes of the distal end of the guide wire.
Figure 14B:
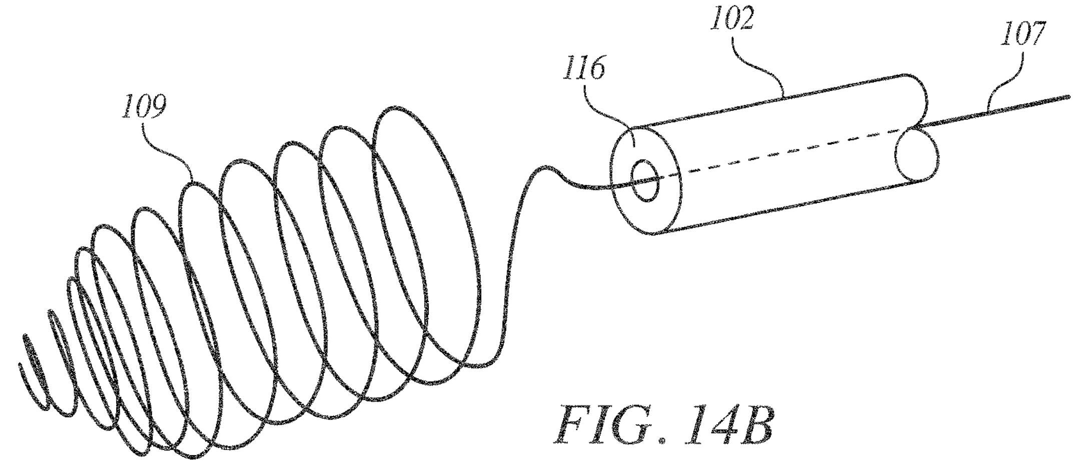

Another embodiment of the present invention is shown in FIGS. 12A-12B and 13 wherein instead of a guide balloon the inventive catheter device 100 includes a wire such as without limitation a memory shape wire. The catheter device 100 may include from about two to about four occluding balloons 104A, 104B, 104C, 104D or even more than five, to control the blood flow in the aorta or other vasculature such as the iliac vasculature. The wire 107 is inserted into the proximal port 110 and pushed within the main lumen 112 or otherwise moved from within the catheter shaft 102 to outside of the distal port 116 such that a distal end 109 is protruding. As shown in FIG. 12A, when the distal end 109 of the wire 107 extends out of the distal port 116 it is straight but depending on the material of the wire 107 the distal end 109 may form a guide. By way of example as shown in FIGS. 12B and 13, the guide shape at the distal end 109 is a corkscrew and as shown in FIGS. 14A and 14B the shape may be a thinner width or thicker width corkscrew shape. Other shapes may be possible and employed which can serve as a guide for the catheter device 100 within the aorta or vasculature such as a spring, pig's tail, triangle, square, circle, or other geometric and non-geometric shapes. Two possible shapes are shown in FIGS. 14A and 14B wherein the width of each shape is different. The shape of the distal end wire 109 is a corkscrew in FIG. 14A which is thinner in width, which is perpendicular to the portion of the wire 107 extending out of the distal port 116, compared to the width of the distal end wire 109 shape in FIG. 14B. The wire 107 may be comprised of flexible materials such as metals or alloys and memory shape metal such as nitinol. Other alloys which exhibit shape memory effects may include brass, bronze, and iron. Such a wire must be made a material compatible with the body as it will be inserted into the aorta and in contact with blood. Other materials may be employed beyond wires, metals or alloys such as polymers and the like.

Figure 15A:
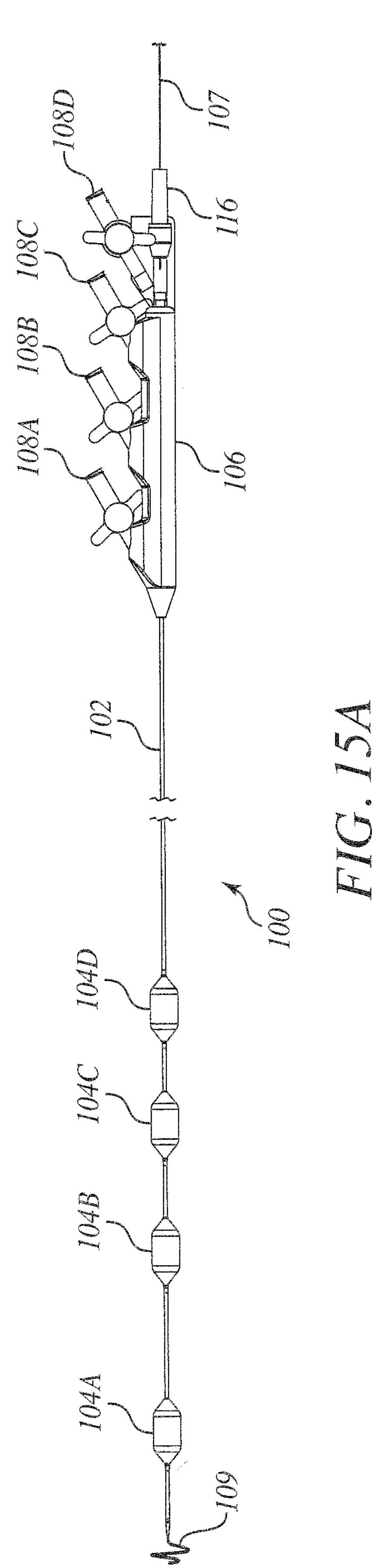
FIG. 15A is a side view of another embodiment of a catheter device in accordance with the present invention including four expandable members and FIG. 15B is an exploded view of the distal end of the catheter including the guide wire and four balloons as the expandable members.
Figure 15B:
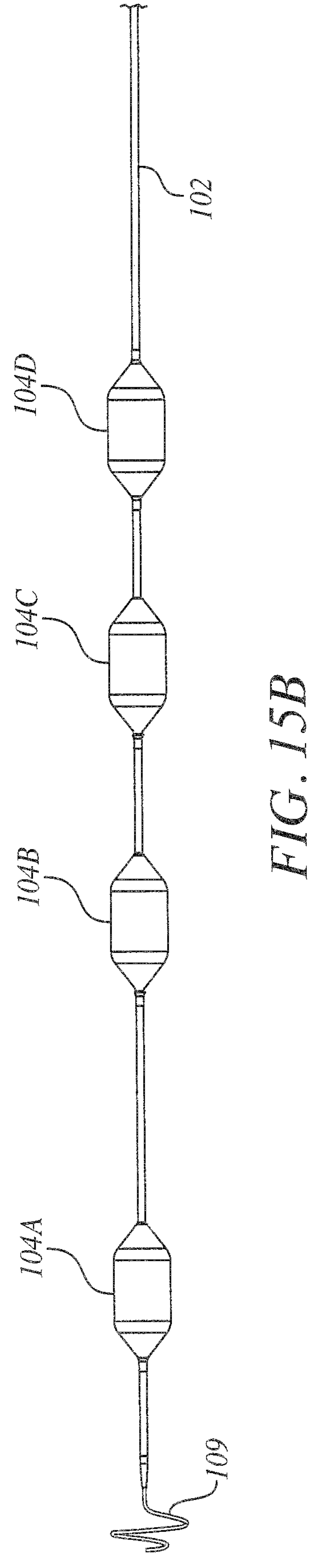

In yet another embodiment of the present invention the catheter device includes a guidewire 108 and four expandable members or balloons as shown in FIGS. 15A and 15B. The device 100 includes a hollow elongate catheter shaft 102 with four distally mounted expandable occlusion balloons 104A, 104B, 104C, 104D in this embodiment and a port along the proximal end of the device 100 including four corresponding turning stopcocks which control the inflation of each of the balloons. The four occlusion balloons in this embodiment are spaced apart along the distal portion of the shaft 102. The spacing between each of the expandable members or balloons may vary depending on the height of the patient in that there may be a smaller distance or larger distance from by way of example the celiac artery 48 and the iliac bifurcation 40. In this embodiment the four expandable members or balloons are in a tubular shape though other geometric shapes may be employed.

Figure 16A:
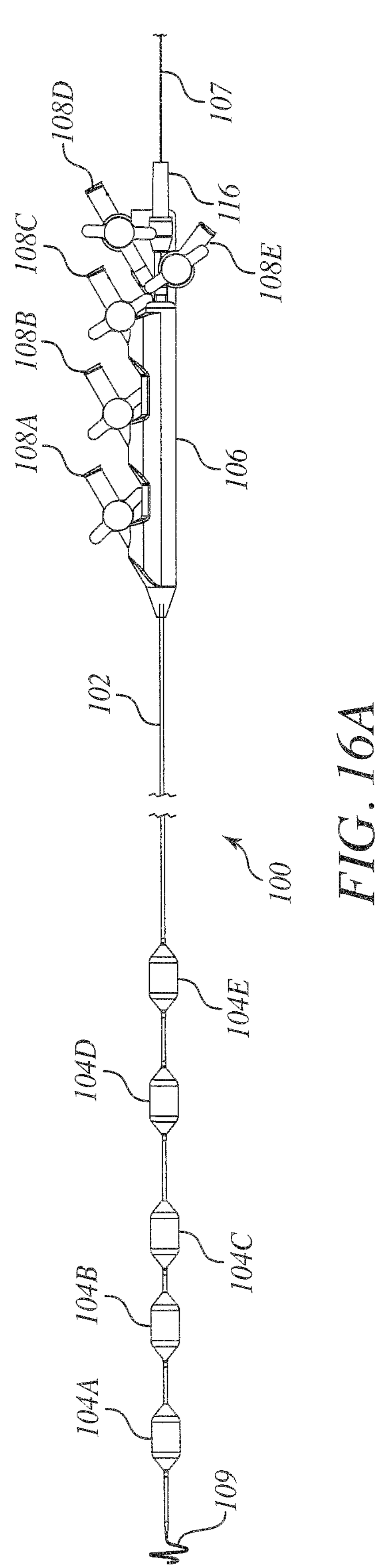
FIG. 16A is a side view of another embodiment of a catheter device in accordance with the present invention including five expandable members and FIG. 16B is an exploded view of the distal end of the catheter including the guide wire and five balloons as the expandable members.
Figure 16B:
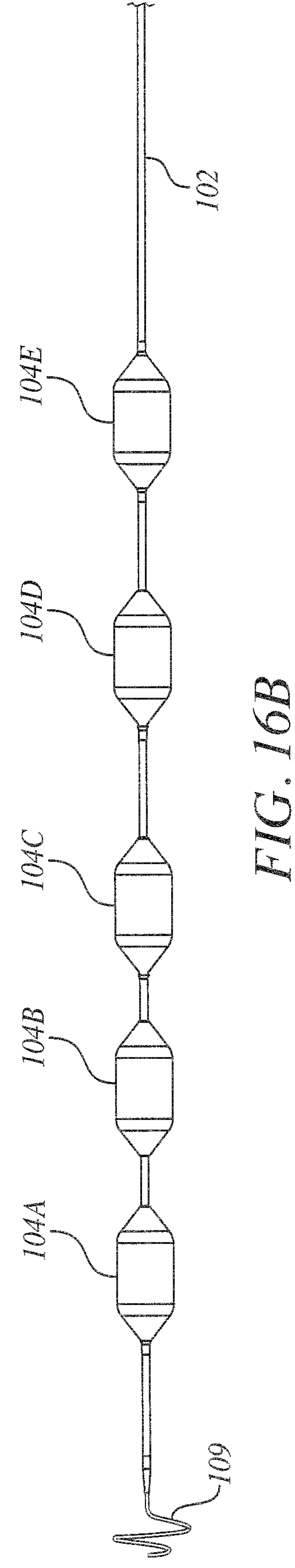

In yet another embodiment of the present invention the catheter device includes a guidewire 108 and four expandable members or balloons as shown in FIGS. 16A and 16B. The device 100 includes a hollow elongate catheter shaft 102 with five distally mounted expandable occlusion balloons 104A, 104B, 104C, 104D, 104E in this embodiment and a port along the proximal end of the device 100 including five corresponding turning stopcocks which control the inflation of each of the balloons. The five occlusion balloons in this embodiment are spaced apart along the distal portion of the shaft 102. The spacing between each of the expandable members or balloons may vary depending on the height of the patient in that there may be a smaller distance or larger distance from by way of example the celiac artery 48 and the iliac bifurcation 40. In this embodiment the five expandable members or balloons are in a tubular shape though other geometric shapes may be employed. In this embodiment the inflation port system 106 is a series of turning or twisting systems which the medical provider uses to manually inflate each expandable member or balloon, though other inflation systems may be employed whether manual or electronic or otherwise.

Figure 17A:
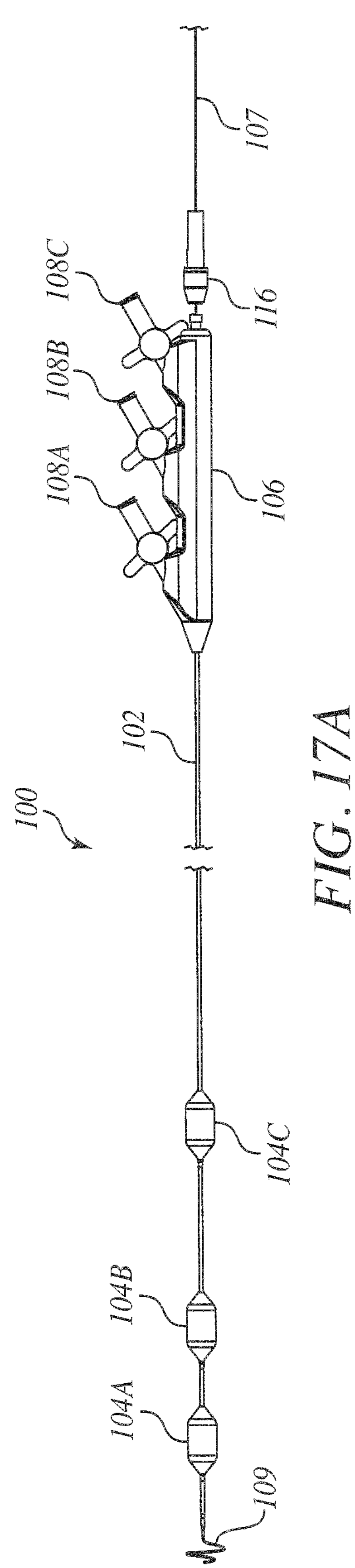
FIG. 17A is a side view of another embodiment of a catheter device in accordance with the present invention including three expandable members and FIG. 17B is an exploded cross-sectional view of the proximal end of the catheter including the inflation ports and the proximal end of the guide wire.
Figure 17B:
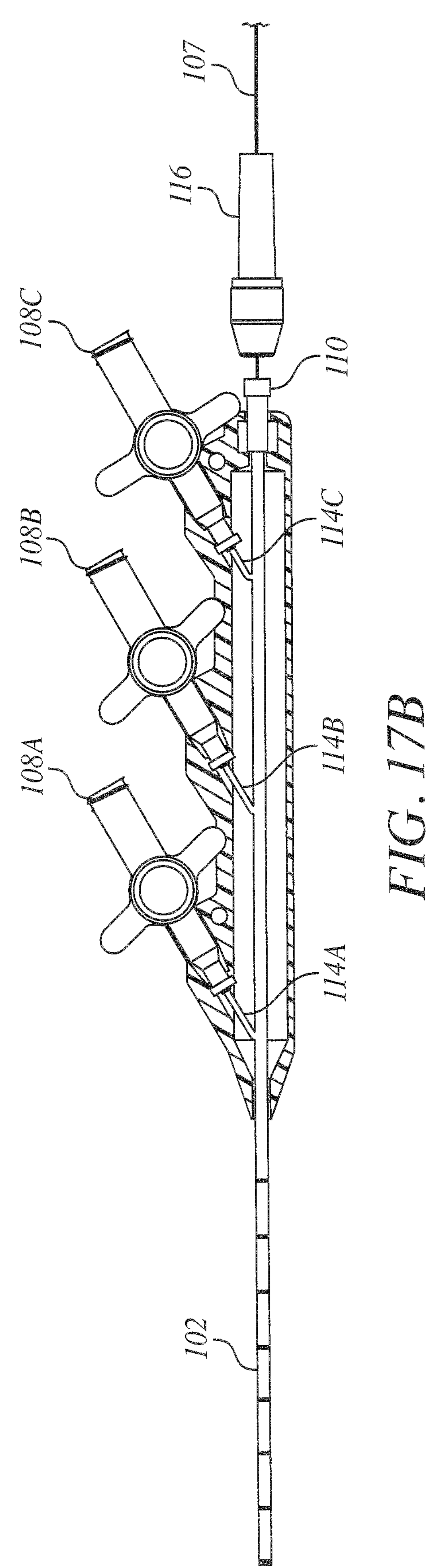

The inflation port in these embodiments is shown in an exploded cross-section in FIG. 17B which is part of the embodiment shown in FIG. 17A including a guide wire 108 and three expandable members or balloons 104A, 104B, 104C. As shown in FIG. 17B, the guide wire 107 is inserted into the main inner lumen 112 at the proximal port 110. The port 106 includes three manual turning stopcocks or ports connected to three inflation lumens 114A, 114B, 114C. The main lumen 112 extends in fluid communication between the main access port 110 and the distal port 116. The first inflation lumen 114A extends in fluid communication between the first port 108A and the balloon 104A. The second inflation lumen 114B extends in fluid communication between the second port 108B and the balloon 104B. The third inflation lumen 114C extends in fluid communication between the third port 108C and the balloon 104C. The three inflation lumens 114A, 114B, 114C allow for independent inflation and deflation of the three balloons 104A, 104B, 104C by pumping a fluid (such as a saline solution or air or other medium) into and from the balloons via the ports 108A, 108B, 108C respectively.

Figure 18A:
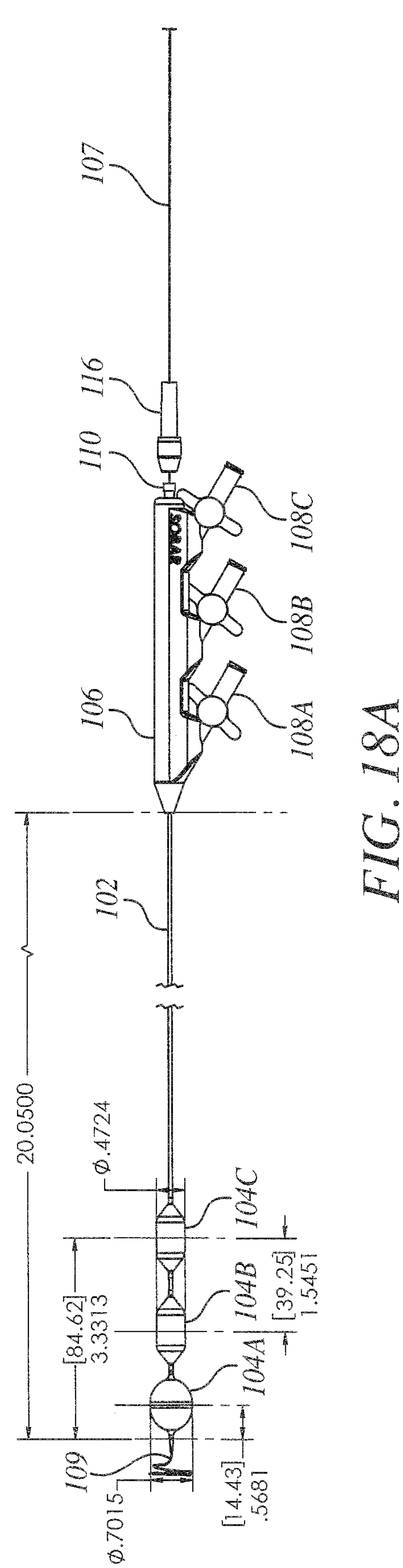
FIGS. 18A-18C are three different embodiments of the device of FIG. 17A with the distal balloon in the shape of a circle with the other two more proximal balloons—in the shape of tubes and the location of each of the three expandable member balloons moved to a different position on the catheter as shown in FIG. 18A compared to FIG. 18B compared to FIB 18C.
Figure 18B:
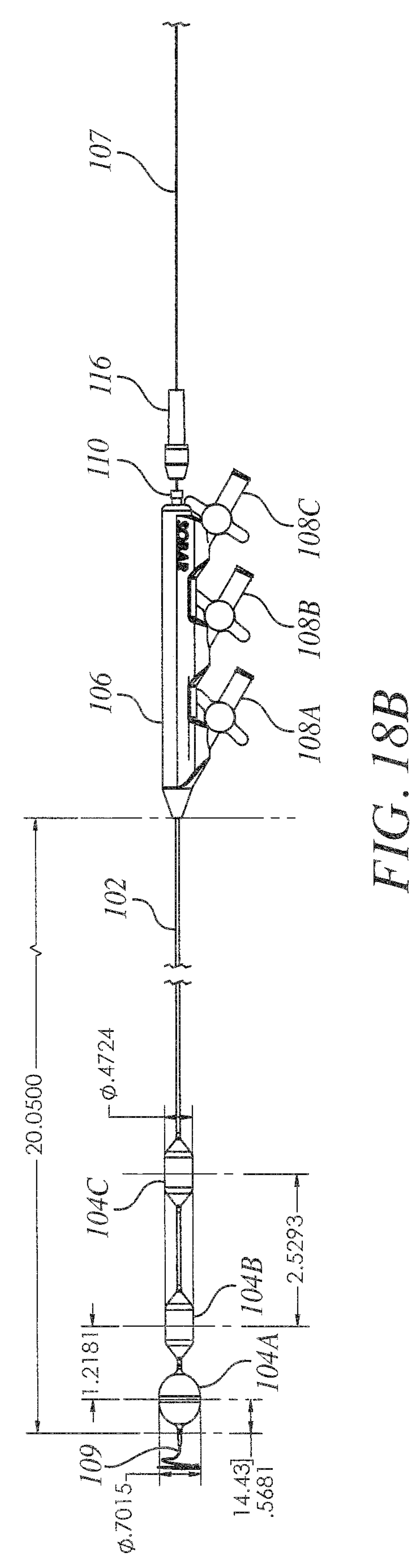
Figure 18C:
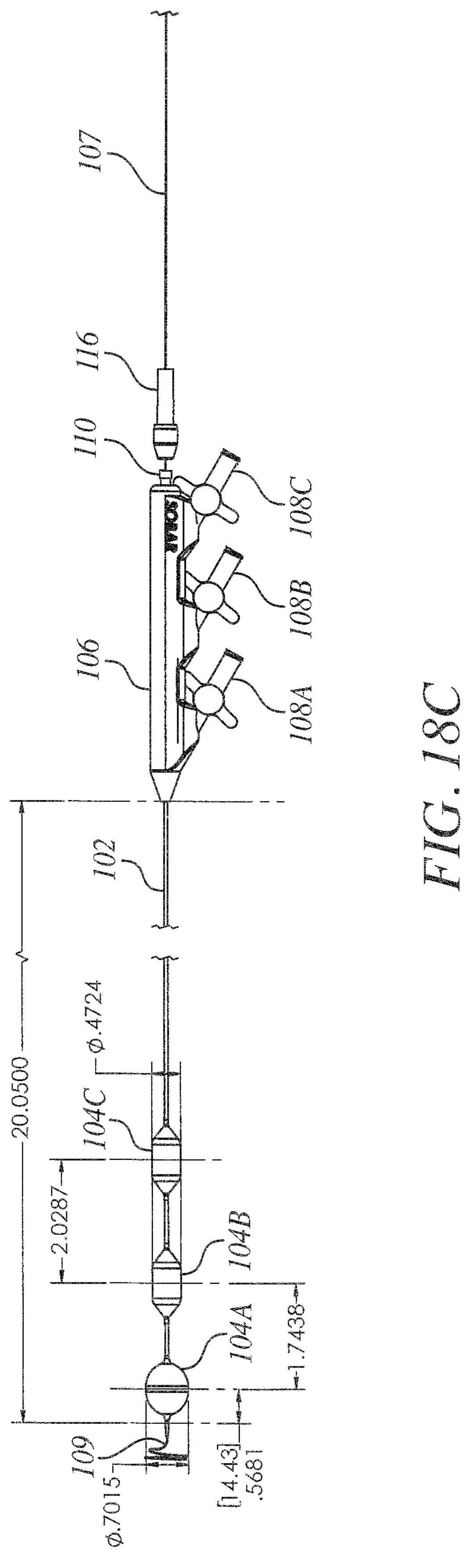

Varying the distance between the expandable members or balloons is possible depending on the artery targeted to be occluded by each balloon and depending on the height of the patient which in turns affects the distance between such arteries on the descending aorta and other vasculature. Different embodiments are shown in FIGS. 18A-18C including a guidewire 107 and three expandable members or balloons 104A, 104B, 104C. Each of these FIGURES shows the device 100 including the guidewire 107 inserted into the proximal port 110 into the inner main lumen 112 and a distal end 109 of the wire 107 extending at the distal end port 116 of the catheter 102 and in the shape of a circle or corkscrew. The distance between the first balloon 104A and second balloon 104B and third balloon 104C in FIG. 17A is shortest of these three embodiments. In FIG. 17B the distance between the first balloon 104A and the second balloon 104B is smaller than the distance between the second balloon 104B and the third balloon 104C. The same is true in FIG. 17C that the distance between the first balloon 104A and the second balloon 104B is smaller than the distance between the second balloon 104B and the third balloon 104C however the distances are different than those shown in FIG. 17B. The distances between each of the balloons, whether two balloons on the catheter or five or more balloons on the catheter, can vary depending on the distance between each of the target arteries to be occluded.

In an embodiment now shown, the balloons themselves can move along the catheter and be adjusted in distance by the user. In this manner less balloons may be needed as each balloon could be used on different arteries as the balloon itself would move along the outer axis of the catheter to occlude different target arteries during the procedure. Additional moving components would be included in these embodiments.

There have been described and illustrated herein several embodiments of an aortic catheter device with a guiding member such as a guide balloon 105 or distal end 109 of guidewire 107 and multiple expanding members such as balloons which are configured to be occluding elements. The balloons can be used in trauma procedures or surgical procedures. Also described herein are multiple methods of operation including using the inventive catheter device for treating hemorrhagic shock as well as an abdominal aortic aneurysm. The inventive catheter device 100 has an advantage of reducing migration of the distal port 116 into visceral arteries and other body openings which in turn reduces complications, bleeding and time during the procedure. Given the trauma and bleeding of the patient at such time, reducing migration, complications, bleeding and time is vital to the success of the procedure. The advantage of multiple occluding balloons 104A, 104B, 104C, 104D also reduce complications, bleeding and time for the procedure. The balloons have an advantage of distance on the catheter corresponding with target arteries to be isolated and occluded. These and other advantages of the inventive catheter device may be added over time.

In yet another embodiment of the present invention, an improved catheter device is shown in FIGS. 19A and 19C configured for use within the iliac bifurcation such as by way of example during a kidney transplantation. The arterial system of the abdomen is shown in FIG. 20. As discussed above during systole, oxygenated blood leaves the heart and enters the aorta where it flows through the ascending aorta and aortic arch (not shown) and down the descending aorta 22. The descending aorta 22 continues to the iliac bifurcation 40, which is a branch that splits into the two common iliac arteries 16A and 16B (shown as 42 in FIGS. 1, 3-6). The descending aorta 22 gives off numerous branches that supply oxygenated blood to the chest cage and the organs within the chest. These branches include the renal arteries 18A, 18B that supply blood to the kidneys 20A, 20B. Ureters 22A, 22B connect the kidneys 20A, 20B to the bladder 24. The iliac arterial vasculature includes two branches continuing from the iliac bifurcation 40. The left branch includes the left common iliac artery 16A, which bifurcates into the left external iliac artery 26A and the left internal iliac artery 28A. When the left external iliac artery 26A passes posterior to the inguinal ligament, it becomes the left femoral artery 30A of the left leg. The right branch of the iliac arterial vasculature includes the right common iliac artery 16B, which bifurcates into the right external iliac artery 26B and the right internal iliac artery 28B. When the right external iliac artery 26B passes posterior to the inguinal ligament, it becomes the right femoral artery 30B of the right leg.

FIGS. 19A and 19B depict a catheter device 200 in accordance with the present invention. The device 200 includes a hollow elongate flexible catheter shaft 202 with four distally mounted expandable balloons 204A, 2048, 204C, 204D. The four balloons are spaced apart along the distal portion of the shaft 202. The distal-most balloon 204A, which is referred to herein as the seating balloon or isolating balloon or anchor balloon is preferably positioned at or near the distal end of the shaft 202 and is expandable to a maximum radial dimension preferably in the range between 0.5 cm and 4.5 cm (most preferably, the maximum radial dimension is 3.0 cm) as shown in FIG. 19C though again many other diameters could be employed. The balloon 204B is proximally located from balloon 204A by a spacing preferably in the range less than about 1 cm and is expandable to a maximum radial dimension preferably in the range between about 1.0 cm and about 1.5 cm as shown in FIG. 2C though other ranges are possible between about 0.5 cm to about 5.0 cm. The balloon 204C is proximally located from balloon 204B by a spacing in the range between about 2.0 cm and about 3.0 cm and is expandable to a maximum radial dimension preferably in the range between about 1.0 cm and about 1.5 cm as shown in FIG. 19C. In its expanded state, the lengthwise dimension L of balloon 204C along the central axis of the catheter shaft 202 is preferably in the range from about 1.0 cm to about 3.5 cm, though other ranges are possible between about 0.5 cm to about 5.0 cm. With the lengthwise dimension of balloon 204C in the range between about 2.0 cm to about 3.5 cm (or longer), the balloon 204D can possibly be omitted from the device so that only three expandable members or balloons are employed. In this manner, balloon 204D is optional and need not be part of all designs and indeed in other embodiments only two expandable members or balloons could be employed, or a fifth expandable member or balloon added. The optional balloon 204D is proximally located from balloon 204C by a spacing preferably in the range between about 1.0 cm and about 2.0 cm and is expandable to a maximum radial dimension preferably in the range between about 1.0 cm and about 1.5 cm as shown in FIG. 19C, though other ranges are possible between about 0.5 cm to about 5.0 cm. The stated ranges of the dimensions and spacing of the balloons 204A, 204B, 204C and 204D correspond to the size and common spacing of the iliac arterial and venous systems as will become evident from the operation of the catheter device 200 as set forth below.

The proximal end of the catheter device 200 is provided with a multi-port adapter 206. The adapter 206 has ports 208A, 208B, 208C, 208D and a main access port 210. The first port 208A is in fluid communication with the balloon 204A. The second port 2088 is in fluid communication with the balloon 204B. The third port 208C is in fluid communication with the balloon 204C. The fourth port 208D is in fluid communication with the balloon 204D. The main access port 210 is in fluid communication with a distal port 216 on the distal end of the catheter shaft 202. The catheter device 200 can be introduced into the vasculature by an introducer sheath as is well known. The catheter shaft 202 can extend through the introducer sheath and be fixated thereto by mechanical means such as a screw in cap or other suitable shaft fixation mechanism.

As shown in FIG. 19B, the hollow elongate catheter shaft 202 has a main inner lumen 212 and four inflation lumens 214A, 214B, 214C, 214D. The main lumen 212 extends in fluid communication between the main access port 210 and the distal port 216. The first inflation lumen 214A extends in fluid communication between the first port 208A and the balloon 204A. The second inflation lumen 214B extends in fluid communication between the second port 208B and the balloon 204B. The third inflation lumen 214C extends in fluid communication between the third port 208C and the balloon 204C. The fourth inflation lumen 214D extends in fluid communication between the fourth port 208D and the balloon 204D. The four inflation lumens 214A, 214B, 214C, 214D allow for independent inflation and deflation of the four balloons 204A, 204B, 204C, 204D by pumping a fluid (such as a saline solution or air or other medium) into and from the balloons via the ports 208A, 208B, 208C, 208D, respectively. In the event that the balloon 204D is omitted from the design, the fourth port 208D and corresponding inflation lumen 214D can also be omitted from the design. In this embodiment the inflation port system 206 is in the form of a trigger system held in the hand of the medical provider such as a surgeon who manually manipulates the inflation of each separate inflation lumen to inflate each separate balloon and to deflate as well. Other inflation port systems may be employed whether manual systems or electronic or other types of systems to inflate and deflate the expandable members or balloons.

The main lumen 212 and the distal port 216 may be used to pass a wide variety of surgical devices (such as guide wires, angioscopes, irrigation lines, vascular grafts and the like) into the vasculature of the patient. The catheter shaft 202 preferably has an external diameter preferably in the range between 5 and 9 french such that it can be introduced into a femoral artery (or a femoral vein) and advanced from below into the descending aorta (or inferior vena cava). The spacing of the balloons 204A, 204B, 204C and 204D along the distal portion of the catheter shaft 202 allows these balloons to be positioned along the iliac arterial (or venous) vasculature. As described below in detail, the fixation balloon 204A is inflated and located at the bifurcation 14 and thus acts to fix the position of the catheter device 200 in the iliac arterial (or venous) vasculature. The other balloons are inflated in order to isolate and occlude blood flow through a portion of the common iliac artery (or vein) traversed by the catheter device 200. This isolated vessel portion can then be used for an anastomosis as part of a kidney transplantation procedure. Such operations will generally require that the length of the catheter shaft 202 be at least 50 cm but could be longer in the range of about 40 cm to about 90 cm.

FIG. 20 illustrates the catheter 200 with the inflatable balloons 204A, 204B, 204C, 204D disposed with the iliac arterial vasculature of a patient. The catheter shaft 202 is introduced into the left femoral artery 30A and advanced through the left external iliac artery 26 and common iliac artery 16A past the iliac bifurcation 14 and into the lower end of the abdominal aorta 12 as shown. The seating balloon 204A is inflated and then the catheter shaft 202 is retracted proximally such that the seating balloon 204A is positioned at the iliac bifurcation 14. In this manner, the seating or anchoring balloon 204A, when inflated, fixes the distal portion of the catheter device 200 in the iliac arterial vasculature as shown. The first balloon 204A can also function to occlude or restrict blood flow from common iliac artery 16A into the iliac bifurcation 14. Preferably, the first balloon 204 does not occlude blood flow from the other common iliac artery 16B. For example, it can be sized such that space remains between the vessel wall of the iliac bifurcation 14 and the balloon 204A to allow blow flow around the balloon. Alternatively, the balloon 204A can provide a flow path through the balloon that allows for blood flow from the common iliac artery 16B to the iliac bifurcation 14.

With the catheter device 200 fixed in position (e.g., with the balloon 204A located at the iliac bifurcation 14), the balloon 2043 is inflated and positioned and sized such in its inflated state it sealably contacts the interior vessel wall of the common iliac artery 16A and occludes blood flow from upstream of the balloon 204B toward the seating balloon 204A at the iliac bifurcation 14. The contact of the inflated balloon 204B to the interior vessel wall of the common iliac artery 16 also acts to fixate and hold the position of the catheter device 200 in the iliac arterial vasculature of the patient. After the balloon 204B is inflated, the balloon 204C and possibly the balloon 204D are inflated and is positioned and sized such in balloon 204C in its inflated state it sealably contacts the interior vessel wall at or near the bifurcation point of the common iliac artery 16A to the left external iliac artery 26A and the left internal iliac artery 26B and occludes blood flow from upstream of the balloon 204C toward the balloon 204B. In the preferred embodiment, the lengthwise dimension of balloon 204C in its expanded state is in the range between about 2.0 cm to 3.5 cm (or longer), which is designed to traverse the entire length of the bifurcation point of the common iliac artery 16A to the left external iliac artery 26A and the left internal iliac artery 26B. In this configuration, it may be possible to omit the balloon 204D. When used, the balloon 204D is positioned and sized such in its inflated state it sealably contacts the interior vessel wall of the left external iliac artery 26A and occludes blood flow from upstream of the balloon 204D toward the balloon 204C. With the balloon 204B in its inflated state and fixing the position of the catheter, the balloon 204A can be deflated as to provide for increased blood flow from the common iliac artery 16B to the iliac bifurcation 14.

In their inflated states, the balloons 204B and 204C isolate and occlude blood flow through the portion of the common iliac artery 16A therebetween. This isolated vessel portion can then be used for an anastomosis 231 to a donor kidney 253 as part of a kidney transplantation procedure. In their inflated states, the balloons 204C and 204D isolate and occlude blood flow through the portion of the left external iliac artery 26A therebetween. This isolated vessel portion can also be used for an anastomosis to a donor kidney as part of a kidney transplantation procedure similar to that shown in FIG. 20. After the anastomosis is complete, the balloons can be deflated and the catheter device 200 retracted and removed from the iliac vasculature.

Advantageously, the catheter device of the present invention can be quickly fixated within the iliac vasculature and manipulated in order to efficiently isolate and occlude a portion of the iliac vasculature (preferably a portion of the common iliac artery or common iliac vein). The fixation of the catheter device within the iliac vasculature can be accomplished without the need for fluoroscopic imaging techniques. The isolation and occlusion of the iliac vasculature provided by the catheter device is suitable for preparing the isolated iliac vascular portion for an anastomosis as part of a kidney transplantation procedure. Such isolation and occlusion are performed in a minimally invasive manner that reduces the risk of bleeding at the occlusion sites (as compared to clamping). It also reduces the risk of dislodging plaque at the occlusion sites (as compared to clamping), and thus reduces the risk of a plaque-induced embolism being carried to the foot or brain, which can cause gangrene in the foot or a stroke in the brain. The catheter device of the present invention can also be used to repair an aortic or abdominal aneurysm. In many cases, such repair involves introduction of a stent through a femoral artery. In some cases, the size of the femoral artery is smaller than the shaft of the stent. In these cases, the surgeon must isolate and clamp an iliac artery in order to a construct a conduit for the stent that is larger than the stent shaft size. The isolation and clamping of the iliac artery require significant dissection and carries a risk of damaging the neighboring tissues. Also, one needs a longer incision to isolate the iliac arteries. The catheter device of the present invention can be used to isolate and occlude a portion of the iliac artery. After such isolation and occlusion, the surgeon can make an incision preferably on the top part of the isolated iliac artery portion. The stent can then be introduced by a conduit through this incision.

There have been described and illustrated herein several embodiments of a catheter device with multiple expandable elements and a method of operating the catheter for efficiently isolating and occluding a portion of the iliac vasculature. While particular embodiments of the invention have been described, it is not intended that the invention be limited thereto, as it is intended that the invention be as broad in scope as the art will allow and that the specification be read likewise. Thus, while particular examples described herein relate to the left branch of the iliac vasculature, the catheter as described herein can be used to isolate and occlude a portion of the right branch of the iliac vasculature and/or the left or right branches of the iliac venous system. Moreover, while particular occluding balloons have been disclosed, it will be appreciated that other occluding elements, such as conical shaped expanding elements or cylindrical-shaped expanding elements, can be used as well. Moreover, the expandable size of such elements can also be controlled by mechanical means such as wires or the like. In addition, while a particular configuration of the multi-lumen catheter shaft has been disclosed, it will be appreciated that other multi-lumen configurations, such as a sequence of concentric lumens formed about the inner guide lumen, can be used. Also, while particular configurations and sizes have been disclosed in reference to elements of the catheter, it will be understood that the aortic catheter described herein can be readily adapted to other configurations and sizes. For example, the device can readily be adapted to include more than four (or less than four) occluding elements and supporting inflation lumens/ports. Also, the outside diameter of the device can readily be adapted to different sizes and distances such that the device is suitable for different size patients, such as a smaller diameter catheter for pediatric patients. Similarly, the distance between balloons can readily be adapted. It will therefore be appreciated by those skilled in the art that yet other modifications could be made to the provided invention without deviating from its spirit and scope as claimed.

The present invention provides a minimally invasive surgical device (and corresponding method of treatment) that enables selective isolation and occlusion of blood flow through the iliac vasculature suitable for preparing a portion of the iliac vascular for an anastomosis as part of a kidney transplantation. It also provides a minimally invasive surgical device (and corresponding method of treatment) that employs a catheter device introduced percutaneously through the femoral vasculature. The inventive catheter device (and corresponding method of treatment) selectively isolates and occludes a portion of one branch of the iliac vasculature while maintaining blood flow through the other branch of the iliac vasculature and through the abdominal vasculature to the heart. In addition, it provides for a minimally invasive surgical device (and corresponding method of treatment) that is quickly and effectively located (e.g., secured in place) in the iliac vasculature of the patient.

While particular embodiments of the invention have been described, it is not intended that the invention be limited thereto, as it is intended that the invention be as broad in scope as the art will allow and that the specification be read likewise. Thus, while particular occluding balloons have been disclosed, it will be appreciated that other occluding elements, such as conical shaped expanding elements or cylindrical-shaped expanding elements, can be used as well. Moreover, the expandable size of such elements can also be controlled by mechanical means such as wires or the like. It is also contemplated that one or more of the occlusion elements can be controlled to partially occlude the aortic passageway. Such partial occlusion may be useful in providing pressure-controlled blood flow to an injured artery after surgically repairing the injured artery. In addition, while a particular configuration of the multi-lumen catheter shaft has been disclosed, it will be appreciated that other multi-lumen configurations, such as a sequence of concentric lumens formed about the inner guide lumen, can be used. Also, while particular configurations and sizes have been disclosed in reference to elements of the aortic catheter, it will be understood that the aortic catheter described herein can be readily adapted to other configurations and sizes. For example, the device can readily be adapted to include more than four (or less than four) occluding elements or balloons and supporting inflation lumens/ports. Also, the outside diameter of the device can readily be adapted to different sizes and distances such that the device is suitable for different size patients, such as a smaller diameter catheter for pediatric patients. Similarly, the distance between balloons can readily be adapted. For example, the distance between the distal-most balloon (e.g., guide balloon 105 or first balloon 104A) and the proximal-most balloon (e.g., the last balloon 104D) may readily be adapted such that it is in the range between 20 and 40 cm. In another example, the distance separating the balloons may be adapted from that described herein such that the balloons are positioned upstream from different arterial groups with the abdominal aorta.

It will therefore be appreciated by those skilled in the art that yet other modifications could be made to the provided invention without deviating from its spirit and scope as claimed. The improved catheter device including a guiding member, whether a balloon or guidewire, and improved balloons on the catheter include many advantages over the known art and conventional devices.

I claim:

1. A method of guiding a catheter device within a vasculature of a patient and occluding a target artery or vasculature, comprising:

a) providing a catheter device for accessing the vasculature of a patient, the catheter device including an elongated hollow housing with a distal end configured to be inserted within a vasculature or aorta of a patient and a proximal end configured to remain outside the patient, and a guidewire comprised of a memory material configured to be inserted within a lumen in the elongated hollow housing in a non-activated flat state and once outside the lumen and distal end of the hollow housing activated into a second state in a shape of either a coil, spiral, corkscrew, circle or other geometric shapes to guide the elongated hollow housing within the vasculature of the patient to a target artery without migrating into non-target arteries, and a plurality of balloons with each balloon connected to a separate lumen within the elongated hollow housing with each lumen connected to an inflation source at the proximal end of said separate lumen, and an inflation port connected to the distal end of the elongated hollow housing and fluidly connected to each separate lumen connected to each balloon;

b) advancing the catheter device, with the guidewire in the activated state and the balloons in a non-inflated state, through the vasculature of a patient such that a distal balloon is positioned at a target artery in the patient; and c) inflating the distal balloon at the location of the target artery so as to isolate or occlude blood flow at the target artery and withdrawing the guidewire from within the elongated hollow housing out of the patient.

2. The method according to claim 1 wherein the plurality of balloons is from 2 to 7 and each balloon has a diameter in an inflated state of about 0.5 cm to about 5.0 cm.

3. The method according to claim 1 wherein each of the plurality of balloons is spaced apart from each other by a distance of about 1.0 cm to about 60 cm.

4. The method according to claim 1 wherein the distance each of the plurality of balloons is spaced is adapted and configured to occlude a target artery or other vasculature selected from the group consisting of renal artery, aortic artery, thoracic artery, abdominal artery, celiac artery, superior mesenteric artery, inferior mesenteric artery, iliac bifurcation, left common iliac artery, left internal iliac artery, left external iliac artery, right common iliac artery, right internal iliac artery, right external iliac artery, left femoral artery, right femoral artery and combinations thereof.

5. The method of claim 1 further comprising surgically affixing a graft into its desired position to bridge the aorta above an abdominal aortic aneurysm within the vasculature and below the abdominal aortic aneurysm.

6. The method of claim 1 further comprising positioning a first balloon so that when inflated it occludes the iliac bifurcation.

7. The method of claim 1 wherein the guidewire is comprised of nitinol and when activated outside of the distal end of the hollow housing has a wider diameter in the perpendicular vertical axis compared to the horizontal axis of the guidewire and hollow housing.

8. The method of claim 1 wherein the plurality of balloons are in the shape of circles, ovals, tubes, rectangles or other geometric shapes and the most distal of the plurality of balloons is spaced at least 40 cm from the most proximal portion of the hollow housing where the hollow housing extends out from the inflation port.

* * * * *